(12) United States Patent
Gerber et al.

(10) Patent No.: US 10,172,991 B2
(45) Date of Patent: Jan. 8, 2019

(54) MODULAR DIALYSATE REGENERATION ASSEMBLY

(71) Applicant: Medtronic, Inc., Minneapolis, MN (US)

(72) Inventors: Martin T. Gerber, Maple Grove, MN (US); Christopher M. Hobot, Tonka Bay, MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 14/644,820

(22) Filed: Mar. 11, 2015

(65) Prior Publication Data

US 2015/0367056 A1 Dec. 24, 2015

Related U.S. Application Data

(60) Provisional application No. 62/016,614, filed on Jun. 24, 2014.

(51) Int. Cl.
*A61M 1/16* (2006.01)
*B01D 15/08* (2006.01)

(52) U.S. Cl.
CPC ........ *A61M 1/1696* (2013.01); *A61M 1/1611* (2014.02); *A61M 1/1613* (2014.02); *B01D 15/08* (2013.01); *A61M 2205/121* (2013.01); *A61M 2205/33* (2013.01)

(58) Field of Classification Search
CPC .......... A61M 1/1696; A61M 2205/121; A61M 2205/33; B01D 15/08
USPC ................ 210/232, 282, 662, 670
See application file for complete search history.

(56) References Cited

U.S. PATENT DOCUMENTS

| | | |
|---|---|---|
| 3,608,729 A | 9/1971 | Haselden |
| 3,669,880 A | 6/1972 | Marantz |
| 3,776,819 A | 12/1973 | Williams |
| 3,850,835 A | 11/1974 | Marantz |
| 3,884,808 A | 5/1975 | Scott |
| 3,902,490 A | 9/1975 | Jacobsen et al. |
| 3,989,622 A | 11/1976 | Marantz |
| 4,094,775 A | 6/1978 | Mueller |
| 4,206,054 A | 6/1980 | Moore |
| 4,209,392 A | 6/1980 | Wallace |
| 4,376,707 A | 3/1983 | Lehmann |
| 4,460,555 A | 7/1984 | Thompson |

(Continued)

FOREIGN PATENT DOCUMENTS

| | | |
|---|---|---|
| CN | 104936633 | 9/2015 |
| EP | 711182 B1 | 6/2003 |

(Continued)

OTHER PUBLICATIONS

PCT/US2015/020044 International Search Report Written Opinion dated Jun. 30, 2015.

(Continued)

*Primary Examiner* — Dirk R Bass

(57) ABSTRACT

A customizable modular dialysate regeneration assembly with connectable sorbent packaging systems. The dialysate regeneration assembly can be customized based on patient parameters or dialysis session parameters. A processor can be included that can determine the correct amount of each sorbent material necessary for a given patient and a given dialysis session.

22 Claims, 16 Drawing Sheets

(56) References Cited

U.S. PATENT DOCUMENTS

| | | |
|---|---|---|
| 4,581,141 A | 4/1986 | Ash |
| 4,650,587 A | 3/1987 | Polak |
| 4,684,460 A | 8/1987 | Issautier |
| 5,230,702 A | 7/1993 | Lindsay et al. |
| 5,284,470 A | 2/1994 | Beltz |
| 5,302,288 A | 4/1994 | Meidl |
| 5,308,315 A | 5/1994 | Khuri |
| 5,507,723 A | 4/1996 | Keshaviah |
| 5,662,806 A | 9/1997 | Keshaviah et al. |
| 5,770,086 A | 6/1998 | Indriksons |
| 5,849,179 A | 12/1998 | Emerson et al. |
| 5,858,186 A | 1/1999 | Glass |
| 5,944,684 A | 8/1999 | Roberts |
| 6,036,858 A | 3/2000 | Carlsson |
| 6,114,176 A | 9/2000 | Edgson et al. |
| 6,126,831 A | 10/2000 | Goldau et al. |
| 6,521,184 B1 | 2/2003 | Edgson et al. |
| 6,572,769 B2 | 6/2003 | Rajan |
| 6,579,460 B1 | 6/2003 | Willis |
| 6,627,164 B1 | 9/2003 | Wong |
| 6,666,840 B1 | 12/2003 | Falkvall et al. |
| 6,719,745 B1 | 4/2004 | Taylor |
| 6,814,724 B2 | 11/2004 | Taylor |
| 6,818,196 B2 | 11/2004 | Wong |
| 6,861,266 B1 | 3/2005 | Sternby |
| 6,878,283 B2 | 4/2005 | Thompson |
| 6,960,179 B2 | 11/2005 | Gura |
| 7,033,498 B2 | 4/2006 | Wong |
| 7,101,519 B2 | 9/2006 | Wong |
| 7,208,092 B2 | 4/2007 | Micheli |
| 7,241,272 B2 | 7/2007 | Karoor |
| 7,276,042 B2 | 10/2007 | Polaschegg |
| 7,326,576 B2 | 2/2008 | Womble et al. |
| 7,435,342 B2 | 10/2008 | Tsukamoto |
| 7,488,447 B2 | 2/2009 | Sternby |
| 7,537,688 B2 | 5/2009 | Tarumi et al. |
| 7,544,300 B2 | 6/2009 | Brugger et al. |
| 7,544,737 B2 | 6/2009 | Poss et al. |
| 7,563,240 B2 | 7/2009 | Gross et al. |
| 7,566,432 B2 | 7/2009 | Wong |
| 7,597,806 B2 | 10/2009 | Uchi |
| 7,794,419 B2 | 7/2010 | Paolini et al. |
| 7,776,210 B2 | 8/2010 | Rosenbaum |
| 7,850,635 B2 | 12/2010 | Polaschegg |
| 7,922,686 B2 | 4/2011 | Childers et al. |
| 7,922,911 B2 | 4/2011 | Micheli |
| 7,947,179 B2 | 5/2011 | Rosenbaum |
| 7,955,290 B2 | 6/2011 | Karoor et al. |
| 7,988,854 B2 | 8/2011 | Tsukamoto |
| 8,002,726 B2 | 8/2011 | Karoor |
| 8,012,118 B2 | 9/2011 | Curtin |
| 8,029,454 B2 | 10/2011 | Kelly et al. |
| 8,066,658 B2 | 11/2011 | Karoor et al. |
| 8,080,161 B2 | 12/2011 | Ding et al. |
| 8,087,303 B2 | 1/2012 | Beavis |
| 8,096,969 B2 | 1/2012 | Roberts |
| 8,180,574 B2 | 5/2012 | Lo et al. |
| 8,187,250 B2 | 5/2012 | Roberts |
| 8,197,439 B2 | 6/2012 | Wang et al. |
| 8,303,532 B2 | 11/2012 | Hamada et al. |
| 8,404,491 B2 | 3/2013 | Li et al. |
| 8,409,444 B2 | 4/2013 | Wong |
| 8,480,607 B2 | 7/2013 | Davies |
| 8,647,506 B2 | 2/2014 | Wong |
| 8,733,559 B2 | 5/2014 | Wong |
| 8,764,981 B2 | 7/2014 | Ding |
| 8,777,892 B2 | 7/2014 | Sandford |
| 9,144,640 B2 | 9/2015 | Pudil |
| 2001/0007931 A1 | 7/2001 | Blatter |
| 2001/0009756 A1 | 7/2001 | Hei et al. |
| 2002/0112609 A1 | 8/2002 | Wong |
| 2003/0080059 A1 | 5/2003 | Peterson et al. |
| 2003/0097086 A1 | 5/2003 | Gura |
| 2003/0105435 A1 | 6/2003 | Taylor |
| 2003/0113931 A1 | 6/2003 | Pan |
| 2003/0114787 A1 | 6/2003 | Gura |
| 2004/0019312 A1 | 1/2004 | Childers et al. |
| 2004/0099593 A1 | 5/2004 | DePaolis |
| 2004/0147900 A1 | 7/2004 | Polaschegg |
| 2004/0168963 A1* | 9/2004 | King ............... B01F 1/0027 210/198.1 |
| 2004/0257409 A1 | 12/2004 | Cheok |
| 2005/0006296 A1 | 1/2005 | Sullivan |
| 2005/0113796 A1 | 5/2005 | Taylor |
| 2005/0150832 A1 | 7/2005 | Tsukamoto |
| 2005/0274658 A1 | 12/2005 | Rosenbaum |
| 2006/0241543 A1 | 10/2006 | Gura |
| 2007/0007208 A1 | 1/2007 | Brugger et al. |
| 2007/0179431 A1 | 8/2007 | Roberts |
| 2007/0213665 A1 | 9/2007 | Curtin |
| 2008/0006570 A1 | 1/2008 | Gura |
| 2008/0051696 A1 | 2/2008 | Curtin |
| 2008/0053905 A9 | 3/2008 | Brugger et al. |
| 2008/0217245 A1 | 9/2008 | Rambod |
| 2009/0020471 A1 | 1/2009 | Tsukamoto |
| 2009/0078636 A1 | 3/2009 | Uchi |
| 2009/0101552 A1 | 4/2009 | Fulkerson |
| 2009/0120864 A1 | 5/2009 | Fulkerson |
| 2009/0157877 A1 | 6/2009 | Baek |
| 2009/0216045 A1 | 8/2009 | Singh |
| 2009/0266358 A1* | 10/2009 | Sacristan Rock ... A61M 16/104 128/203.26 |
| 2010/0004588 A1 | 1/2010 | Yeh |
| 2010/0007838 A1 | 1/2010 | Fujimoto |
| 2010/0078381 A1 | 4/2010 | Merchant |
| 2010/0084330 A1 | 4/2010 | Wong |
| 2010/0100027 A1* | 4/2010 | Schilthuizen ....... A61M 1/1696 604/6.09 |
| 2010/0101195 A1 | 4/2010 | Clements |
| 2010/0102190 A1 | 4/2010 | Zhu et al. |
| 2010/0114012 A1 | 5/2010 | Sandford et al. |
| 2010/0217181 A1 | 8/2010 | Roberts |
| 2010/0224492 A1 | 9/2010 | Ding et al. |
| 2010/0314314 A1 | 12/2010 | Ding |
| 2011/0009798 A1 | 1/2011 | Kelly |
| 2011/0017665 A1 | 1/2011 | Updyke |
| 2011/0048949 A1 | 3/2011 | Ding et al. |
| 2011/0163034 A1 | 7/2011 | Castellarnau |
| 2011/0171713 A1 | 7/2011 | Bluchel |
| 2011/0184340 A1 | 7/2011 | Tan |
| 2011/0272352 A1 | 11/2011 | Braig |
| 2011/0297593 A1 | 12/2011 | Kelly |
| 2011/0315611 A1* | 12/2011 | Fulkerson ........... A61M 1/3639 210/96.2 |
| 2012/0018377 A1 | 1/2012 | Tsukamoto |
| 2012/0095402 A1 | 4/2012 | Lande |
| 2012/0248017 A1 | 10/2012 | Beiriger |
| 2013/0018095 A1 | 1/2013 | Vath |
| 2013/0019179 A1 | 1/2013 | Zhao |
| 2013/0027214 A1 | 1/2013 | Eng |
| 2013/0028809 A1 | 1/2013 | Barton |
| 2013/0199998 A1 | 8/2013 | Kelly |
| 2013/0213890 A1 | 8/2013 | Kelly |
| 2013/0213891 A1 | 8/2013 | Karoor |
| 2014/0001112 A1 | 1/2014 | Karoor |
| 2014/0138294 A1 | 5/2014 | Fulkerson |
| 2014/0190885 A1 | 7/2014 | Meyer |
| 2014/0251908 A1 | 9/2014 | Ding |
| 2014/0326671 A1 | 11/2014 | Kelly |
| 2015/0057602 A1 | 2/2015 | Mason |
| 2015/0108609 A1 | 4/2015 | Kushida |
| 2015/0144539 A1 | 5/2015 | Pudil |
| 2015/0144542 A1* | 5/2015 | Pudil ............... B01D 15/203 210/87 |
| 2015/0157960 A1 | 6/2015 | Pudil |
| 2015/0238673 A1 | 8/2015 | Gerber |
| 2015/0250937 A1 | 9/2015 | Pudil |
| 2015/0258266 A1 | 9/2015 | Merchant |
| 2015/0306292 A1 | 10/2015 | Pudil |
| 2015/0367051 A1 | 12/2015 | Gerber |
| 2015/0367052 A1 | 12/2015 | Gerber |
| 2015/0367056 A1 | 12/2015 | Gerber |
| 2015/0367057 A1 | 12/2015 | Gerber |

(56) References Cited

U.S. PATENT DOCUMENTS

| | | |
|---|---|---|
| 2015/0367058 A1 | 12/2015 | Gerber |
| 2015/0367059 A1 | 12/2015 | Gerber |
| 2015/0367060 A1 | 12/2015 | Gerber |

FOREIGN PATENT DOCUMENTS

| | | |
|---|---|---|
| EP | 1701752 A2 | 9/2006 |
| EP | 1592494 B1 | 6/2009 |
| EP | 2575827 A2 | 12/2010 |
| EP | 2576453 A2 | 12/2011 |
| EP | 1545652 B1 | 1/2013 |
| EP | 1345856 B1 | 3/2013 |
| EP | 2344220 B1 | 4/2013 |
| EP | 1345687 | 6/2013 |
| EP | 1 991 289 B1 | 6/2015 |
| WO | 9532010 A1 | 11/1995 |
| WO | 0185295 A2 | 11/2001 |
| WO | 2003043677 A2 | 5/2003 |
| WO | 2003051422 A2 | 6/2003 |
| WO | 2004064616 A2 | 8/2004 |
| WO | 2004062710 A3 | 10/2004 |
| WO | 2005123230 A2 | 12/2005 |
| WO | 2007089855 A2 | 8/2007 |
| WO | WO 20070103411 | 9/2007 |
| WO | 2008075951 A1 | 6/2008 |
| WO | 2009157877 A1 | 12/2009 |
| WO | 2009157878 A1 | 12/2009 |
| WO | 2010028860 A1 | 3/2010 |
| WO | 2010102190 A4 | 11/2010 |
| WO | 2010141949 | 12/2010 |
| WO | 2013019179 | 2/2013 |
| WO | 2013019179 A1 | 2/2013 |
| WO | 2013025957 | 2/2013 |
| WO | 2013027214 | 2/2013 |
| WO | 2013028809 A3 | 2/2013 |
| WO | WO 2013/028809 | 2/2013 |
| WO | 2013019994 A3 | 4/2013 |
| WO | 2012060700 | 5/2013 |
| WO | 2013025844 A3 | 5/2013 |
| WO | 2013101888 | 7/2013 |
| WO | 2013103607 A1 | 7/2013 |
| WO | 2013103906 | 7/2013 |
| WO | 2015142624 | 9/2015 |
| WO | 2015199764 | 12/2015 |

OTHER PUBLICATIONS

PCT/US2015/020044 Written Opinion dated Jun. 21, 2016.
PCT/US2015/020044 International Preliminary Report on Patentability dated Nov. 4, 2016.
PCT/US2015/020044 International Search Report dated Jun. 30, 2015.
PCT Application, PCT/US20013/020404, filed Jan. 4, 2013.
U.S. Application, U.S. Appl. No. 13/836,973, filed Mar. 15, 2013.
U.S. Application, U.S. Appl. No. 14/259,655, filed Apr. 23, 2014.
U.S. Application, U.S. Appl. No. 14/259,589, filed Apr. 23, 2014.
PCT/US2014/065950 International Search Report and Written Opinion dated Feb. 24, 2015.
PCT/US2015/032492 International Search Report dated Nov. 19, 2015.
PCT/US2015/016270 International Search Report and Written Opinion dated Jun. 5, 2015.
PCT/US2015/016273 International Search Report and Written Opinion dated Jun. 9, 2015.
PCT/US2015/032492 Written Opinion dated Nov. 19, 2015.
PCT/US2015/020046 International Search Report and Written Opinion dated Jun. 29, 2015.
International Search Report from PCT/US2012/051946.
U.S. Appl. No. 61/526,209.
U.S. Appl. No. 13/757,693, filed Jan. 4, 2013.
U.S. Appl. No. 13/836,079, filed Mar. 15, 2013.
U.S. Appl. No. 14/240,129, filed Aug. 22, 2013.
U.S. Appl. No. 13/835,735, filed Mar. 15, 2013.
PCT/US15/18587 International Preliminary Report on Patentability dated Jun. 6, 2016.
Office Action for Chinese Application No. 201580009562.5 dated Jul. 3, 2017.
International Preliminary Report on Patentability for Application No. PCT/US2015/032492 dated Jun. 30, 2017.
European Search Report for App. No. 15751391.2 dated Aug. 4, 2017.
Supplementary European Search Report for EP15812252.3 date of completion dated Jan. 24, 2018 (2 pages).

* cited by examiner

MODULAR DIALYSATE REGENERATION ASSEMBLY

FIELD OF THE INVENTION

The invention relates to sorbent packaging and related systems providing for dialysate regeneration customized to specific patients, related packaging systems including sorbent pouches and related assemblies, and methods of use. The sorbent packaging systems and assemblies can be configured to provide a therapeutically and cost-optimized treatment based on an appropriate selection of sorbent and related amounts of the sorbent material for use during a dialysis session using a modular system based on modular, interchangeable sorbent compartments.

BACKGROUND

Sorbent cartridges are commonly designed to hold and store various sorbent materials. The known sorbent cartridges are generally of a fixed sized and pre-determined shape and cannot be re-configured or customized for personalized use once manufactured. In particular, the sorbent cartridges are rigid and do not allow for adjustment and cannot be altered. As such, a user cannot configure an amount of sorbent materials to optimize use of the materials based on a patient condition, for example state of uremia or weight. The lack of customization prevents the possibility of reducing consumable expense because known sorbent cartridges are one-size-fits-all. Existing sorbent cartridges fail to account for patient needs and do not allow for fewer or additional materials to be added or taken away depending on a patient's initial blood chemistry profile or the amounts of each contaminant that need to be removed. Static sorbent configurations also prevent economical disposal and/or recycling as well as regeneration of the sorbent materials.

Larger patients or patients who are more uremic may need greater amounts of particular sorbent materials to properly regenerate dialysate used in sorbent dialysis, such as zirconium phosphate. Often, sorbent cartridges are constructed in a standardized manner so that they may be used in a standardized dialysis machine. This means that each patient receives the same amount of each sorbent material. Standardized sorbent cartridges therefore can either contain too much of a particular sorbent material, adding to waste and driving up costs, or the sorbent cartridge may contain the correct amount for an average patient, meaning the capacity to regenerate dialysate will be exceeded for patients requiring more of the sorbent material. The individual sorbent compartments of the present invention allow for customization of the sorbent cartridge, thus reducing cost and waste.

Therefore, there is a need for a modular system of interchangeable sorbent housings or compartments that can utilize different weights and sizes for storing various sorbent materials of different shapes, weights, and sizes, and allowing for the creation of a customized system with interchangeable modular sorbent configurations customizable to dialysis or patient parameters. There is also a need for a device and system that can be configured to interchangeably fit a system of modular sorbent compartments.

There is also a need for facilitating ease of packaging and shipping using a modular interchangeable system to house sorbent materials. To combat counterfeiting, there is a need for isolating individual vendors from a sorbent manufacturing process wherein specific sorbent materials used for dialysis can be pre-filled separately. There is a need for providing an option for allowing sub-vendors to manufacture sorbent housing or separate assembly line fill production facilities from one another. There is also a need for providing a customized sorbent system wherein different layers of sorbent materials can be used together in sorbent compartments wherein each sorbent compartment is modular and interchangeable. There is also a need for reducing final assembly steps required in preparing a dialysis system for use. There is also a need for pre-filling a component housing sorbent materials at precise quantities to avoid user error.

There is also a need for a modular sorbent cartridge having the features of reduced size and weight necessary for a portable dialysis machine. There is further a need for sorbent modules that allow for easy customization regarding the amount of material within the modules based on the needs of a particular patient or dialysis session.

SUMMARY OF THE INVENTION

The first aspect of the invention relates to a modular dialysate regeneration assembly. In any embodiment of the first aspect of the invention, the modular dialysate regeneration assembly can comprise one or more sorbent compartment containing at least one sorbent material. The sorbent compartment can be attachable to another sorbent compartment to form a modular dialysate regeneration assembly. The modular dialysate regeneration assembly can have a desired dialysate regeneration profile based on one or more dialysis parameters and/or one or more patient parameters.

In any embodiment of the first aspect of the invention, the one or more sorbent compartment can have one or more size wherein any sized sorbent compartment is attachable to any other sized sorbent compartment.

In any embodiment of the first aspect of the invention, at least one of the one or more sorbent compartments can have a circular or rectangular planar base having a wall extending perpendicularly and upwardly from said base defining an internal area, and a circular or substantially rectangular planar top matching the planar base. The sorbent compartment can have an engagement configuration selected from any one of: the base cooperatively engaging with the top of another sorbent compartment and the top cooperatively engaging with the base of another sorbent compartment; the base not cooperatively engaging with the top of another sorbent compartment and the top cooperatively engaging with the base of another sorbent compartment; the base cooperatively engaging with the top of another sorbent compartment and the top not cooperatively engaging with the base of another sorbent compartment; and the base not cooperatively engaging with the top of another sorbent compartment and the top not cooperatively engaging with the base of another sorbent compartment.

In any embodiment of the first aspect of the invention, the one or more sorbent compartment can be selected from any combination or number of compartments from the selected group of: a first sorbent compartment having a sorbent weight ranging from 0.1 kg to 0.5 kg; a second sorbent compartment having a sorbent weight ranging from 0.5 kg to 1.0 kg; a third sorbent compartment having a sorbent weight ranging from 1.0 kg to 1.5 kg; a fourth sorbent compartment having a sorbent weight ranging from 1.5 kg to 2.0 kg; a fifth sorbent compartment having a sorbent weight ranging from 2.0 kg to 2.5 kg; a sixth sorbent compartment having a sorbent weight ranging from 2.5 kg to 3.0 kg; a seventh sorbent compartment having a sorbent weight ranging from 3.0 kg to 3.5 kg; an eighth sorbent compartment having a sorbent weight ranging from 3.5 kg to 4.0 kg; a ninth sorbent compartment having a sorbent weight ranging from 4.0 kg to 4.5 kg; a tenth sorbent compartment having a sorbent weight ranging from 4.5 kg to 5.0 kg; and an eleventh sorbent compartment having a sorbent weight ranging from 0.0001 kg to 0.1 kg.

In any embodiment of the first aspect of the invention, the one or more sorbent compartment can be selected from any combination or number of compartments from the selected group of: a first sorbent compartment having a volume ranging from 0.25 L to 1.3 L; a second sorbent compartment having a volume ranging from 1.3 L to 2.5 L; a third sorbent compartment having a volume ranging from 2.5 L to 3.7 L; a fourth sorbent compartment having a volume ranging from 3.7 L to 5.0 L; a fifth sorbent compartment having a volume ranging from 5.0 L to 6.3 L; a sixth sorbent compartment having a volume ranging from 6.3 L to 7.5 L; a seventh sorbent compartment having a volume ranging from 7.5 L to 10 L; an eighth sorbent compartment having a volume ranging from 0.01 L to 0.25 L; and a ninth sorbent compartment having a volume ranging from 0.001 L to 0.01 L.

In any embodiment of the first aspect of the invention, the at least one sorbent compartment can have a planar base with upwardly extending walls connecting to a planar top. The walls can be constructed from a rigid, fluid impermeable material.

In any embodiment of the first aspect of the invention, the base and top can be circular and the upwardly extending walls can slope inward to an axis of the compartment wherein the top can have a smaller surface area than the base, or the upwardly extending walls can slope outward from the axis wherein the top can have a larger surface area than the base.

In any embodiment of the first aspect of the invention, the base and top can be rectangular and can have four upwardly extending walls sloping inward to an axis of the compartment wherein the top can have a smaller surface area than the base, or four upwardly extending walls can slope outward from the axis wherein the top can have a larger surface area than the base.

In any embodiment of the first aspect of the invention, the modular dialysate regeneration assembly can further comprise an engagement member disposed on and extending upwardly from the planar top of the sorbent compartment.

In any embodiment of the first aspect of the invention, the modular dialysate regeneration assembly can further comprise a receiving groove disposed on the planar base of the sorbent compartment for receiving an engagement member.

In any embodiment of the first aspect of the invention, the modular dialysate regeneration assembly can further comprise an engagement member disposed on and extending downwardly from the planar base of the sorbent compartment.

In any embodiment of the first aspect of the invention, the modular dialysate regeneration assembly can further comprise a receiving groove disposed on the planar top of the sorbent compartment for receiving an engagement member.

In any embodiment of the first aspect of the invention, the sorbent materials can be selected from the group comprising activated carbon, ion-exchange resin, hydrous zirconium oxide, alumina, urease, a mixture of alumina and urease, zirconium phosphate, and any combination thereof.

In any embodiment of the first aspect of the invention, the one or more dialysis parameters and/or one or more patient parameters can be selected from the group comprising patient weight, concentration of one or more compound in a blood sample from a patient, previous dialysate results of the patient, dialysis rate, length of dialysis session, a level of impurities in the water used, an expected amount of infusates to be added, and combinations thereof.

In any embodiment of the first aspect of the invention, the modular dialysate regeneration assembly can be part of a controlled compliant dialysis circuit.

In any embodiment of the first aspect of the invention, the one or more sorbent compartment can be a sorbent pouch configurable into a stacked assembly of sorbent pouches wherein each of the sorbent pouches can be constructed in-part of a porous material forming the sorbent pouch containing inside at least one sorbent material wherein the porous material can allow fluid to pass through the sorbent pouch and substantially retains at least one sorbent material in the sorbent pouch.

In any embodiment of the first aspect of the invention, the porous material can form in-part a sorbent pouch containing at least one sorbent material, the porous material allowing fluid to pass through the sorbent pouch. In any embodiment, the sorbent pouch can be formed wholly from the porous material. The porous material can also allow fluid to pass through the sorbent pouch and can substantially retain the one sorbent material in the sorbent pouch. The porous material can in certain embodiments retain greater than 98% by weight of the sorbent material. In any embodiment, the porous material can also be flexible.

In any embodiment of the first aspect of the invention, the sorbent pouch can be constructed from a material selected from the group comprising bolting cloth, porous polymer, porous metal, cotton, ashless filter paper, Dacron, and polyethylene terephthalate.

In any embodiment of the first aspect of the invention, the porous material can retain greater than 98% by weight of the sorbent material.

In any embodiment of the first aspect of the invention, the dialysate regeneration profile can be based on dialysate parameters obtained from a patient.

In any embodiment of the first aspect of the invention, each sorbent compartment can be a distinct color depending on the sorbent material contained within the sorbent compartment.

In any embodiment of the first aspect of the invention, at least one sorbent compartment can contain urease and at least one sorbent compartment can contain zirconium phosphate, wherein the engagement configuration can be such that the compartment containing urease can connect to the compartment containing zirconium phosphate, wherein the compartment containing urease is positioned immediately before the compartment containing zirconium phosphate; and wherein the engagement configuration is such that the top of the compartment containing urease cannot cooperatively engage with any sorbent compartment except the sorbent compartment containing zirconium phosphate and the bottom of the compartment containing zirconium phosphate cannot cooperatively engage with any sorbent compartment except the sorbent compartment containing urease.

In any embodiment of the first aspect of the invention, each of the one or more sorbent compartments comprising the modular dialysate regeneration assembly can comprise sidewalls having a thickness different from the sidewall thicknesses of the other sorbent compartments, such that the one or more sorbent compartments can have differing interior diameters.

In any embodiment of the first aspect of the invention, each sorbent compartment can have a sidewall thickness greater than that of the previous sorbent compartment in series.

In any embodiment of the first aspect of the invention, each of the one or more sorbent compartments comprising the modular dialysate regeneration assembly can have differing exterior diameters.

In any embodiment of the first aspect of the invention, each sorbent compartment can have an exterior diameter smaller than that of the previous sorbent compartment in series.

In any embodiment of the first aspect of the invention, the one or more sorbent compartments can each contain one or more annular ring, wherein the one or more annular ring can be constructed from a fluid impermeable substance, and wherein the one or more annular ring can be disposed on the interior circumference of each of the one or more sorbent compartments and can extend radially into the center of each of the one or more sorbent compartments.

In any embodiment of the first aspect of the invention, the annular ring can have a cross-sectional shape selected from the group comprising circular, triangular, and rectangular.

Any of the features disclosed as being part of the first aspect of the invention can be included in the first aspect of the invention, either alone or in combination.

The second aspect of the invention relates to a method that can comprise creating a dialysate regeneration profile based on patient and/or dialysate parameters; selecting one or more modular sorbent compartment based on the dialysate regeneration profile; and attaching the one or more modular sorbent compartment for use during a dialysis session.

In any embodiment of the second aspect of the invention, the method can further comprise inputting patient and/or dialysis parameters into a processor, wherein the processor can determine the number of each sorbent compartment and/or the size of each sorbent compartment necessary for a dialysis session.

In any embodiment of the second aspect of the invention, the patient parameters can be selected from the group consisting of patient weight, concentration of components in the patient blood, and previous dialysis results for the patient, and combinations thereof.

In any embodiment of the second aspect of the invention, the dialysis parameters can be selected from the group consisting of dialysate rate, an expected amount of infusates to be added, a level of impurities in the water used during the dialysis session, length of dialysis session, and combinations thereof.

In any embodiment of the second aspect of the invention, the patient and/or dialysate parameters can be obtained from a sensor, said sensor in fluid communication with fluid flowing out from at least one of the modular sorbent compartments, the sensor being capable of sensing the presence and/or concentration of at least one compound in the fluid.

DETAILED DESCRIPTION OF THE INVENTION

Figure 1:
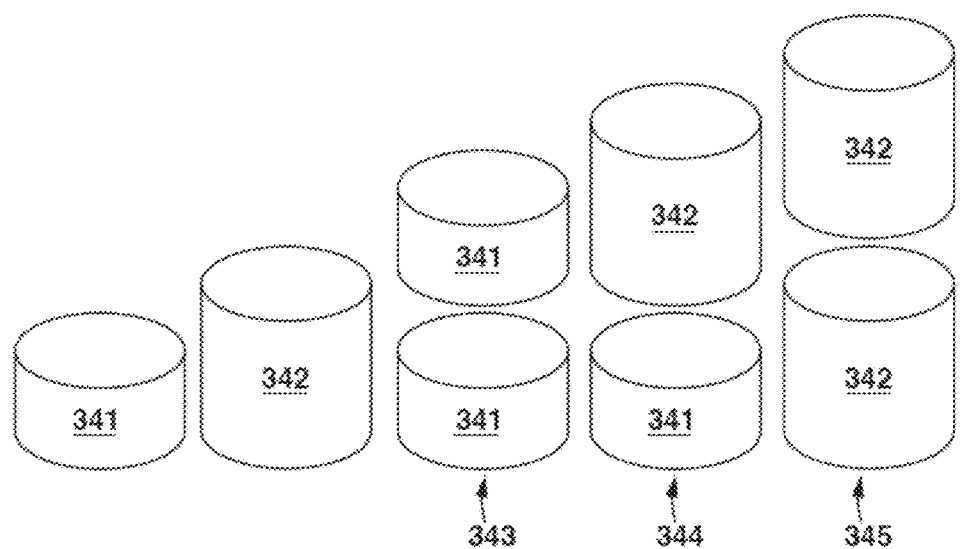
FIG. 1 shows how sorbent compartments of various sizes can be combined to create a customized dialysate regeneration system.

Unless defined otherwise, all technical and scientific terms used herein generally have the same meaning as commonly understood by one of ordinary skill in the relevant art.

The articles "a" and "an" are used herein to refer to one or to more than one (i.e., to at least one) of the grammatical object of the article. By way of example, "an element" means one element or more than one element.

An "adhesive" is any substance known in the art for use in affixing one surface to another surface, or to seal two surfaces together.

"Ammonia detector" refers to any apparatus that is capable of detecting the presence or concentration of ammonia or ammonium ions in a fluid.

An "annular ring" is a ring having a substantially circular shape. The cross-section of the ring may be rectangular, triangular, round, or any other known shape. The ring may be constructed of any rigid or semi-rigid material, and may be adhered to the inner surface of a sorbent pouch by any means known in the art. An annular ring may also be an "o-ring."

The term "attachable" refers to two or more components that can be combined such that a physical connection is created between the two or more components.

An "axis of the pouch" describes an imaginary line running vertically down the center of the sorbent pouch, situated in the center of the surface of the sorbent pouch when viewed from the top perspective.

The term "cartridge" refers to any container designed to contain a powder, liquid, or gas made for ready connection to a device, structure, system, flow path or mechanism. The container can have one or more compartments. Instead of compartments, the container can also be comprised of a system of two or more modules connected together to form the cartridge wherein the two or more modules once formed can be connected to a device, structure, system, flow path or mechanism.

A "circular shape" describes a sorbent pouch constructed in a generally round shape having the form of a circle. This term is not intended to limit the shape of the sorbent pouch to any particular size or dimensions, and may encompass oval or oblong configurations as well.

A "compartment" means a part or a space designated, defined, marked or partitioned off from a structure. For example, a urease compartment in a sorbent cartridge is a space defined within the sorbent cartridge containing urease. Optionally, the compartment can be in selected fluid communication with other compartments or modules of the sorbent system. The compartment can be physically separated or marked off without a physical barrier.

The term "comprising" includes, but is not limited to, whatever follows the word "comprising." Thus, use of the term indicates that the listed elements are required or mandatory but that other elements are optional and may or may not be present.

A "connector" as used herein forms a fluid connection between two components wherein fluid or gas can flow from one component, through the connector, to another component. It will be understood that the connector provides for a fluid connection in its broadest sense and can include any type of tubing, fluid or gas passageway, or conduit between any one or more components of the invention.

The term "consisting of" includes and is limited to whatever follows the phrase "consisting of." Thus, the phrase indicates that the limited elements are required or mandatory and that no other elements may be present. The term "consisting essentially of" includes whatever follows the term "consisting essentially of" and additional elements, structures, acts or features that do not affect the basic operation of the apparatus, structure or method described.

"Cooperatively engaging" describes two compartments that have complementary engagement members that allow for an engagement configuration. "Not cooperatively engaging" describes two compartments that do not have complementary engagement members such that an engagement configuration is not possible.

The term "detachable" or "detached" relates to any component of the present invention that can be separated from a system, module, sorbent pouch, cartridge or any component of the invention. "Detachable" can also refer to a component that can be taken out of a larger system with minimal time or effort. In certain instances, the components can be detached with minimal time or effort, but in other instances can require additional effort. The detached component can be optionally reattached to the system, module, cartridge or other component. A detachable module can often be part of a reusable module.

"Dialysate" is the fluid that passes through the dialyzer on the side of the dialysis membrane that is opposite to the fluid (e.g. blood) that is being dialyzed.

A "dialysate regeneration profile" is a profile matched to a particular selection of sorbent materials. For example, the amount of urease and zirconium phosphate a patient requires can be selected based on the patient's pre-dialysis blood urea nitrogen (BUN) levels. The amount of zirconium phosphate and/or ion-exchange resin a patient needs can also be based on the patient's pre-dialysis levels of calcium, magnesium, and potassium. The amount of zirconium oxide a patient needs can be based on the patient's pre-dialysis level of phosphates. The amount of activated carbon a patient requires can be based on the patient's pre-dialysis levels of creatinine or trend in monthly lab values. The amount of zirconium phosphate, activated carbon, ion-exchange resin and hydrous zirconium oxide required can also be selected based on the levels of various solutes in the water used for dialysis.

"Dialysis" is a type of filtration, or a process of selective diffusion through a membrane. Dialysis removes solutes of a specific range of molecular weights via diffusion through a membrane from a fluid to be dialyzed into a dialysate. During dialysis, a fluid to be dialyzed is passed over a filter membrane, while dialysate is passed over the other side of that membrane. Dissolved solutes are transported across the filter membrane by diffusion between the fluids. The dialysate is used to remove solutes from the fluid to be dialyzed. The dialysate can also provide enrichment to the other fluid.

"Dialysis parameter(s)" are any factors of a dialysis session that tend to affect the amount of sorbent material needed for the dialysis session.

A "disc-like shape" describes a sorbent pouch forming a flat, circular shape, as in a compressed cylinder. This definition is not intended to limit the dimensions or radius of the sorbent pouch, and may therefore encompass discs having an oval shape, and discs of any radial width or thickness.

A "double layer of material" describes a second layer of material of the same or smaller area than the primary layer of material, disposed on the surface of the primary layer of material forming a surface of a sorbent pouch. The material used to form the double layer can be the same or different from the material forming the primary layer. Any rigid or flexible porous material known in the art is contemplated.

An "elastomer" or "elastomeric material" is a material comprising a polymer having high elasticity, such that the material may be easily stretched and shaped to be adapted to an internal cavity defined by a sorbent cartridge or other compartment.

"Engagement configuration" is a type of configuration that describes whether a particular compartment engages with another compartment.

"Engagement members" allow compartments to cooperatively engage. In certain embodiments, these engagement members may be clasps or latches. In one embodiment, an engagement member allows for coupling of a top portion and a bottom portion of a sorbent pouch that can be opened and resealed.

"Expected amount of infusates" refers to the amount of any infusate, or multiple infusates, that are expected to be added to the dialysate during a dialysis session. For example, in one embodiment, the expected amounts of infusates might include 0-4.0 mEq/L calcium, 0-3 mEq/L potassium, and 0-4.0 mEq/L magnesium. In practice, the expected amount of infusates may vary based on dialysis rate and length of dialysis session.

"Flow" refers to the movement of a fluid or gas.

A "fluid" is a liquid substance optionally having a combination of gas and liquid phases in the fluid. Notably, a liquid, as used herein, can therefore also have a mixture of gas and liquid phases of matter.

The term "fluid communication" refers to the ability of fluid or gas to move from one component or compartment to another within a system or the state of being connected, such that fluid or gas can move by pressure differences from one portion that is connected to another portion.

A "fluid impermeable material" is any material through which fluid cannot pass.

The term "fluidly connectable" refers to the ability of providing for the passage of fluid or gas from one point to another point. The two points can be within or between any one or more of compartments, modules, systems, sorbent pouches, components, and rechargers, all of any type.

"Immobilized," as used to refer to a chemical component, refers to a configuration wherein a chemical component is held in place by some force. The force may be provided by absorption, adsorption, adhesion, or any other method for the chemical to be held in place.

The term "immobilizing sorbent material" refers to the process of a sorbent material being placed onto another material, such that the sorbent material is held in place by some force. The force may be provided by absorption, adsorption, adhesion, or any other method for the chemical to be held in place.

The term "impregnated" describes any process known to a person of ordinary skill in the art by which a material may be caused to absorb or be saturated with a substance. In one embodiment, the material forming a sorbent pouch may be impregnated with an anticoagulant, such that the surface of the sorbent pouch absorbs the anticoagulant.

"Impurities in water" refers to ionic or non-ionic compounds in the water that are removable by the sorbent materials in a sorbent cartridge.

"Infusate" is a solution of one or more salts for the adjustment of the composition of a dialysate.

A "modular dialysate regeneration assembly" is one or more sorbent compartment containing at least one sorbent material attached to at least another sorbent compartment.

"Module" refers to a discreet component of a system. Each of the modules can be fitted to each other to form a system of two or more modules. Once fitted together, the modules can be in fluid connection and resist inadvertent disconnection. A single module can represent a cartridge to be fitted to a device or mechanism if the module is designed to contain all the necessary components for an intended purpose such as a sorbent for use in dialysis. In such a case, the module can be comprised of one or more compartments within the module. Alternatively, two or more modules can form a cartridge to be fitted to a device or mechanism where each module individually carries separate components but only when connected together contain in summation all the necessary components for an intended purpose such as a sorbent for use in dialysis. A module can be referred to as a "first module," "second module," "third module," etc. to refer to any number of modules. It will be understood that the designation of "first," "second," "third," etc. does not refer to the respective placement of the module in the direction of fluid or gas flow, and merely serves to distinguish one module from another unless otherwise indicated.

"One or more size" of a sorbent compartment describes a compartment that can be any size but which is also attachable to another compartment regardless of differences in size.

An "o-ring seal member" is a mechanical gasket having a ring shape; it is a loop of elastomer or other suitable material known in the art with a round cross-section, designed to be seated in a groove and compressed during assembly between two or more parts, creating a seal at the interface. In one embodiment, an o-ring seal member may be used to seal the interface between a sorbent pouch and a sorbent cartridge such that fluid is directed through, rather than around, the sorbent pouch.

The terms "pathway," "conveyance pathway," "fluid flow path," and "flow path" refer to the route through which a fluid or gas, such as dialysate or blood, travels.

"Patient parameters" are any physiological factors of a particular patient that tend to affect the amount of sorbent material for a given dialysis session with that patient.

A "porous material" may describe any suitable porous material known in the art from which a sorbent pouch may be constructed. For example, the porous material can include, but is not limited to, bolting cloth, porous polymer, porous metal, cotton, ashless filter paper, Dacron and polyethylene terephthalate. The porous material chosen for individual sorbent pouches may be selected based upon specific porosity in view of the sorbent material to be contained within the sorbent pouch.

A "porous structure" describes a sorbent pouch being formed of a porous material, wherein the sorbent pouch can be manipulated to fit an internal cavity defined by a sorbent cartridge.

A "planar top" or "planar base" is a surface perpendicular to the axis of the urease pouch culminating at the uppermost portion of the upwardly extending walls of a urease pouch, or a flat surface culminating at the bottommost portion of the downwardly extending walls of a urease pouch, respectively. The planar top may be any geometric shape and dimensions complementary to the upwardly extending walls of the urease pouch, for example round, square, triangular or rectangular. A circular planar top or planar base is a flat surface having a circular shape, while a rectangular planar top or planar base is a flat surface having a square or rectangular shape.

A "pouch," or a "sorbent pouch," as used herein, can mean any porous container that is constructed, in-part or wholly, having any shape and being made of any material as described herein, containing at least one sorbent material and allowing fluid to pass through the pouch. For example, a pouch may have a disc-like shape, having rigid side walls and porous, flexible upper and lower surfaces, such that fluid is allowed to flow through the lower and upper surfaces of the pouch, but does not pass through the side walls of the pouch. Alternatively, the pouch may be rectangular or triangular in shape. The pouch may be made entirely of flexible porous material, or may be formed of entirely rigid, partially porous material. The pouch may be formed in dimensions correlating directly to the cartridge into which the pouch is inserted, such that the edges of the pouch are flush with the interior surface of the cartridge. Alternatively, the pouch may be formed of a flexible material with dimensions slightly larger than those of the interior of the cartridge, such that a seal is formed between the pouch and the interior surface of the cartridge. In another embodiment, the pouch may be formed in dimensions smaller than that of the interior of the cartridge, such that the pouch may be simply placed in the cartridge. A pouch may be formed of bolting cloth, porous polymer, porous metal, cotton, ashless filter paper, Dacron, polyethylene terephthalate, or any other flexible or rigid, permeable or semi-permeable material.

"Recharging" refers to the process of treating spent sorbent material to restore the functional capacity of the sorbent material, so as to put the sorbent material back into a condition for reuse or for use in a new dialysis session. In some instances, the total mass, weight and/or amount of "rechargeable" sorbent materials remain the same. In other embodiments, the total mass, weight and/or amount of "rechargeable" sorbent materials may change. Without being limited to any one theory of invention, the recharging process may involve exchanging ions bound to the sorbent material with different ions, which in some instances may increase or decrease the total mass of the system. However, the total amount of the sorbent material will in some instances be unchanged by the recharging process. Upon a sorbent material undergoing "recharging," the sorbent material can then be said to be "recharged." Recharging of rechargeable sorbent materials is not the same as replenishing of a particular sorbent material such as urease.

The term "recyclable" refers to material that can be reused.

"Reusable" refers in one instance to a material that can be used more than one time, possibly with treatment or recharging of the material between uses. Reusable may also refer to a cartridge that contains a material that can be recharged by recharging the material(s) contained within the cartridge.

A "rigid structure" describes a sorbent pouch being formed of inflexible material such that the sorbent pouch cannot be manipulated and reshaped to be adapted to an internal cavity defined by a sorbent cartridge, but instead maintains its shape.

A "semi-rigid structure" describes a sorbent pouch having surfaces that can be flexed, but that are substantially rigid unless force is applied to cause the surfaces to flex.

A "sensor" is a component capable of determining the states of one or more variables in a system. In one embodiment, a sensor may be capable of sensing the presence and/or concentration of at least one compound in the fluid flowing through at least one sorbent pouch, using any means known in the art.

A "separator" is a layer of flexible or rigid material positioned within a sorbent pouch that divides the sorbent pouch into top and bottom portions, such that sorbent materials housed in the top and bottom portions, respectively, do not come in contact with each other. The separator is formed of a porous material such that spent dialysate or other liquid may flow between the top and bottom portions of the sorbent pouch through the separator, but such that the sorbent materials housed in the top and bottom portions of the sorbent pouch cannot pass through the separator.

A "sewn stitch" is a method of sealing two surfaces together using a needle and a thread composed of any material known in the art.

A "sorbent assembly shell" is an empty sorbent cartridge housing into which a stacked sorbent assembly is inserted.

"Sorbent cartridge" refers to a cartridge that can contain one or more sorbent materials. The cartridge can be connected to a dialysis flow path. The sorbent materials in the sorbent cartridge are used for removing specific solutes from solution, such as urea. The sorbent cartridge can have a single compartmental design wherein all sorbent materials necessary for performing dialysis are contained within the single compartment. Alternatively, the sorbent cartridge can have a modular design wherein the sorbent materials are dispersed across at least two different modules, which can be connected to form a unitary body. Once the at least two modules are connected together, the connected modules can be referred to as a sorbent cartridge, which can be fitted to a device or mechanism. When a single module contains all the sorbent materials necessary for performing dialysis, the single module can be referred to as a sorbent cartridge.

"Sorbent materials" are materials capable of removing specific solutes from solution, such as urea or urea byproducts.

The term "sorbent pouch" refers to a structure that contains at least one sorbent material, and is constructed from a material that can allow fluid to freely pass through the pouch while substantially retaining the sorbent material inside.

"Sorbent weight" is the physical weight of the sorbent material inside a sorbent compartment or sorbent pouch.

"Spent dialysate" is a dialysate contacted with blood through a dialysis membrane and containing one or more impurities, or waste species, or waste substance, such as urea.

A "square" or "rectangular" shape can describe a sorbent compartment or sorbent pouch having four edges and four angles. This description is not intended to limit the size and dimensions of the sorbent compartment or sorbent pouch, and may therefore encompass sorbent compartments and sorbent pouches having angles greater than or less than ninety degrees, and with edges of differing lengths with respect to each other.

The term "substantially," is used in conjunction with a term to describe a particular characteristic. For example, as used in the phrase "substantially retains the at least one sorbent material in the sorbent pouches," the term describes the ability to retain a sorbent material or particles characterized by an average pore diameter such that a significant amount of the material or particles are retained within the sorbent pouch.

A "threaded fitting" is a fitting for connecting two components wherein the male portion has a helical ridge wrapped around a cylinder, and the female portion is a cylindrical hole with internal helical ridges so that when the male portion is screwed into the female portion the two components are locked together.

A "triangular shape" describes a sorbent pouch having three edges and three corners, wherein the edges and corners may vary in length and degree individually and with respect to each other.

A "twist-lock fitting" is a fitting for connecting two components wherein the male portion of the fitting contains a head with a length exceeding its width, the female portion of the fitting is a hole with a length that exceeds its width and is larger than the male portion, so that when the male portion is inserted into the female portion and either portion is twisted the two components become locked together.

"Upwardly extending walls" describe the surfaces extending radially outward from the top and bottom surfaces of a sorbent pouch or sorbent compartment. For example, in a sorbent compartment or sorbent pouch having a disc-like shape, the circular top and bottom portions of the sorbent compartment or sorbent pouch are connected by the rounded upwardly extending wall of the sorbent compartment or sorbent pouch. The upwardly extending walls may be of any shape or dimensions complementary to the corresponding top and bottom portions of the sorbent compartment or sorbent pouch. In the case of a triangular shaped sorbent compartment or sorbent pouch, the upwardly extending walls would extend from a bottom portion of the sorbent compartment or sorbent pouch and culminate at a vertex, in the absence of a top portion.

Modular Dialysate Regeneration Assembly

The first and second aspects of the invention provide a modular dialysate regeneration assembly of interchangeable sorbent compartments that can be connected or attached to each other for use during sorbent dialysis. The modular system allows for any one of the sorbent compartments to be reconfigured with any number of similarly or differently sized or weighted sorbent compartments according to a desired dialysate regeneration profile. The different compartments can be individually selected and mounted in various positions and orientations. Each modular sorbent compartment can selectively perform a function necessary for performing dialysis such as removing specific toxins from the spent dialysate, either completely, or by replacing them with non-toxic material.

In any embodiment of the first or second aspect of the invention, the sorbent compartments of the first or second aspect of the invention may be sorbent pouches. Sorbent pouches are made of a material that allows fluid to pass through the sorbent pouch, but which does not allow sorbent material to pass out of the sorbent pouch, as will be explained herein. In any embodiment of the first or second aspect of the invention, the sorbent compartments can be rigid, fluid impermeable containers. The containers can be connected to each other by fluid connectors to allow dialysate to pass from one rigid container to the next rigid container.

The system can use sorbent pouches or rigid containers in order to create a configuration of sorbent materials that can be modified depending on the needs of the patient. For example, any number of modular sorbent compartments represented by sorbent pouches or rigid containers of different sizes, weights and shapes can be arranged together, permitting a user to customize the sorbent material configuration based on a patient's weight or uremic state. The modular sorbent system can include multiple differently sized and/or weighted modular compartments for holding different types and quantities of sorbent materials. This allows for the creation of a personalized, adjustable sorbent system to perform a particular dialysis session optimized in terms of sorbent usage that can result in both reduced cost and improved patient outcomes.

In any embodiment of the first or second aspect of the invention, the sorbent compartments may come in standard sizes. These sizes may be smaller than those used for an average patient. For example, as shown in FIG. 1, zirconium phosphate compartments may have two sizes. One sized compartment 341 can, for example, contain 3.1 kg of sorbent material. Another sized compartment 342 may contain 4.2 kg of material. By using only single compartments, a total zirconium phosphate amount of 3.1 kg or 4.2 kg of material can be used. However, by combining two sorbent compartments, total zirconium phosphate amounts of 6.2 kg 343, 7.3 kg 344, or 8.4 kg 345 are possible. The actual amount of sorbent material in any particular sorbent compartment is flexible. In any embodiment of the first or second aspect of the invention, for example, a single size of 1 kg may be used. By stacking sorbent compartments together, total sorbent materials can be utilized in 2 kg, 3 kg, 4 kg and so on, allowing for an easily customizable system. In any embodiment of the first or second aspect of the invention, the one or more sorbent compartments can be have a first sorbent weight ranging from 0.1 kg to 0.5 kg; a second sorbent compartment having a sorbent weight ranging from 0.5 kg to 1.0 kg; a third sorbent compartment having a sorbent weight ranging from 1.0 kg to 1.5 kg; a fourth sorbent compartment having a sorbent weight ranging from 1.5 kg to 2.0 kg; a fifth sorbent compartment having a sorbent weight ranging from 2.0 kg to 2.5 kg; a sixth sorbent compartment having a sorbent weight ranging from 2.5 kg to 3.0 kg; a seventh sorbent compartment having a sorbent weight ranging from 3.0 kg to 3.5 kg; an eighth sorbent compartment having a sorbent weight ranging from 3.5 kg to 4.0 kg; a ninth sorbent compartment having a sorbent weight ranging from 4.0 kg to 4.5 kg; a tenth sorbent compartment having a sorbent weight ranging from 4.5 kg to 5.0 kg; and an eleventh sorbent compartment having a sorbent weight ranging from 0.0001 kg to 0.1 kg. The system can determine, based on the patient's needs, the necessary number of sorbent compartments for a dialysis session, as will be explained herein.

Figure 2:
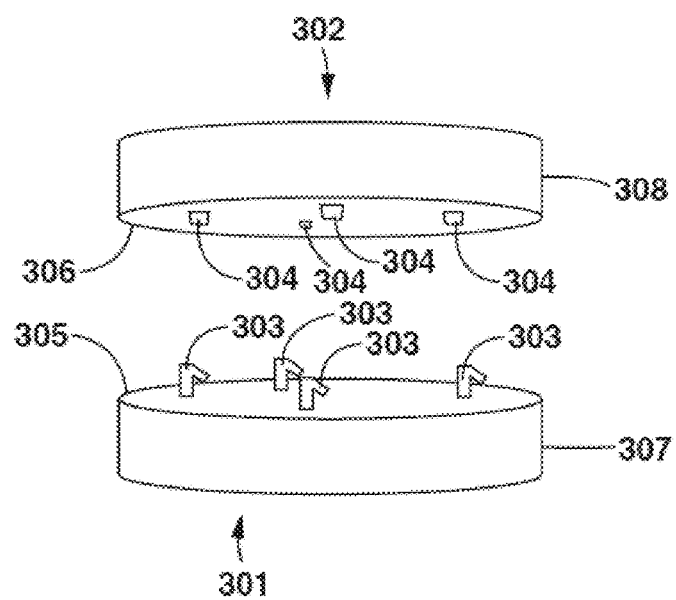
FIG. 2 is a perspective view of two sorbent compartments with the ability to connect directly together.

In any embodiment of the first or second aspect of the invention where the sorbent compartments are sorbent pouches, the sorbent pouches may be made with fluid-impermeable side walls. The side walls may be made out of metal or any other fluid-impermeable material known in the art. In any embodiment of the first or second aspect of the invention where the sorbent pouches themselves are made out of porous plastic or metal, the side walls may be made out of the same substance without pores. In any embodiment of the first or second aspect of the invention where the top and bottom layers of the sorbent pouches are made out of a fluid permeable substance, such as fabric, the side walls of the sorbent pouches may be made out of a fluid impermeable substance. In any embodiment of the first or second aspect of the invention, the sorbent pouches themselves may connect together directly to create a stacked assembly, eliminating the need for an external housing. In any such embodiment of the first or second aspect of the invention, the sorbent pouches themselves can constitute the sorbent cartridge. In any embodiment of the first or second aspect of the invention, as shown in FIG. 2, the top and bottom layers of the sorbent pouch can have a means for connecting to another sorbent pouch. For example, first sorbent pouch 301 can have engagement members 303 on the top surface of the sorbent pouch 301. Second sorbent pouch 302 can have engagement members 304 on the bottom surface of the sorbent pouch 302. Engagement members 303 of the first sorbent pouch 301 and engagement members 304 of the second sorbent pouch 302 can engage in any known fashion to seal the two sorbent pouches together. O-ring 305 on the first sorbent pouch 301 and o-ring 306 on the second sorbent pouch 302 can create a water-tight seal when the two sorbent pouches are connected, eliminating any leaks from the interface. Because the side wall 307 of the first sorbent pouch 301 and the side wall 308 of the second sorbent pouch 302 are impermeable to fluid, there will be no leakage from the sides of the structure either. In this way, the sorbent pouches of the invention can fit together without the need for containment in an external sorbent cartridge.

The engagement members 303 and 304 can be constructed in any known fashion to create a sealed structure. In FIG. 2, they are shown as a twist lock fitting. The engagement members 303 can fit into the holes serving as engagement members 304. When the sorbent pouches are twisted in opposing directions, the engagement members 303 can turn relative to the holes 304. This creates a construct wherein the top portion of engagement members 303 cannot fit back out of the holes 304. In order to separate the sorbent pouches, the sorbent pouches must be twisted back in the opposite direction so that the tops of engagement members 303 can once again fit through the holes 304 and allow for easy disengagement. Any other known method of connecting the first sorbent pouch 301 and the second sorbent pouch 302 is contemplated by the first or second aspect of the invention, and may be used to connect three, four, or any number of sorbent pouches together in series.

In any embodiment of the first or second aspect of the invention, the engagement members can be configured so as to ensure proper sequencing of the sorbent pouches. For example, a zirconium phosphate sorbent pouch must be placed downstream of a sorbent pouch containing urease in order to ensure removal of the ammonia created by the breakdown of urea in the urease sorbent pouch. Accordingly, engagement members on the zirconium phosphate and urease sorbent pouches may be configured such that the zirconium phosphate sorbent pouch is prevented from being connected upstream of the urease sorbent pouch. In any embodiment of the first or second aspect of the invention, this can be accomplished by using engagement members for the urease sorbent pouch and the zirconium phosphate sorbent pouch that are of a different size or shape than the engagement members on other sorbent pouches. In any embodiment of the first or second aspect of the invention, the individual pouches may be colored or marked to indicate the proper sequencing of sorbent pouches. Sorbent pouch coloring can also be used to indicate complete engagement of two or more sorbent pouches together. For example, a sorbent pouch containing zirconium phosphate may be colored red, a sorbent pouch containing urease may be colored blue, a sorbent pouch containing activated carbon may be yellow, and a sorbent pouch containing hydrous zirconium oxide may be green. The user can be instructed to place the sorbent pouches in the order of yellow, then green, then blue, and then red. In any embodiment of the first or second aspect of the invention, the user can be instructed only to place the blue sorbent pouch before the red sorbent pouch if the order of the other sorbent pouches is not critical.

First sorbent pouch 301 can also have engagement members similar to engagement members 304 disposed on the bottom surface of the first sorbent pouch 301 (not shown) to facilitate the attachment of another sorbent pouch before the first sorbent pouch 301. Similarly, second sorbent pouch 302 can have engagement members similar to engagement members 303 disposed on the top surface of the second sorbent pouch 302 (not shown) to facilitate the attachment of another sorbent pouch after the second sorbent pouch 302.

Figure 3:
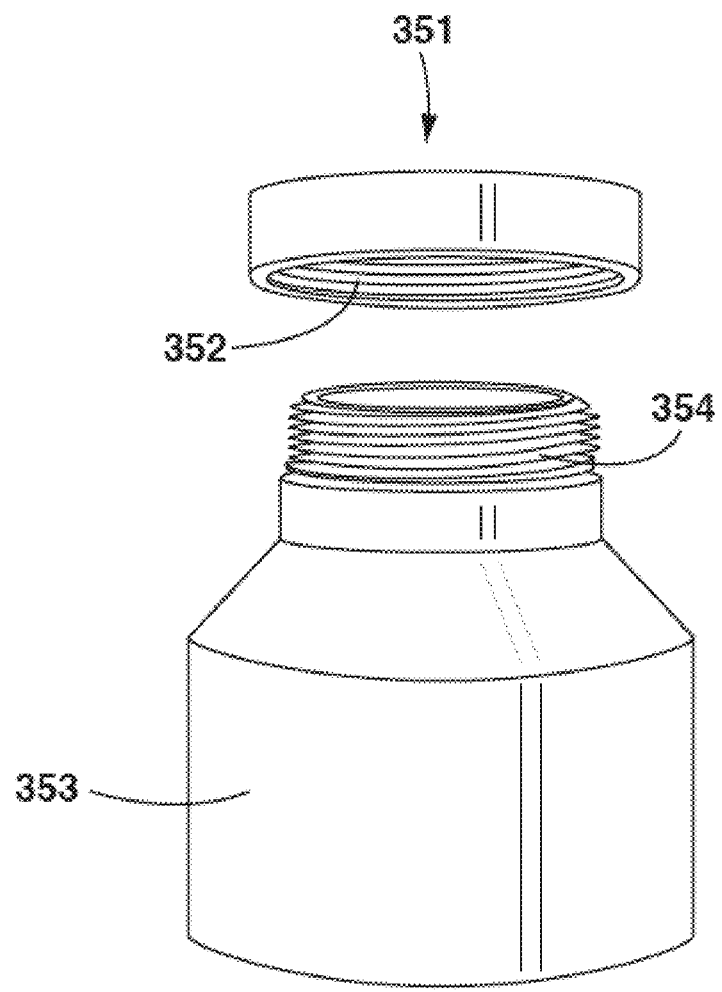
FIG. 3 is a perspective view of a sorbent compartment with a dialysis machine connector.

In order to facilitate connection of the sorbent pouch assemblies of the invention to a dialysis machine, in any embodiment of the first or second aspect of the invention, a dialysis machine connector can be used as shown in FIG. 3. The connector 353 can connect to the first and last sorbent pouches 351 of a sorbent pouch assembly. The connections can be made in any known fashion, including those described above. In FIG. 3, the connection is shown as a threaded connection. The threaded portion 354 of the connector 353 has a circumference such that the connector 353 can fit into the sorbent pouch 351. The threaded portion 354 of the connector 353 can fit into the female threaded portion 352 disposed on the inner circumference of the sorbent pouch 351. Twisting the connector 353 will screw the threaded portion 354 of the connector 353 into the female threaded portion 352 disposed on the inner circumference of sorbent pouch 351, creating a seal and allowing dialysate to enter or exit the sorbent pouch 351 out of or into the dialysis machine. The end of the connector 353 opposite the threaded portion 354 can connect to dialysate tubing (not shown) that can run from the dialysis membrane (not shown) to the connector 353. The same connection can be formed on the opposite side of the sorbent assembly.

In any embodiment of the first or second aspect of the invention, the first and last sorbent pouches in a stacked sorbent assembly can comprise connector portions to connect to the dialysis machine connector on one side of the sorbent pouch and connector portions to connect to the other sorbent pouches in the stacked assembly on the opposite side of the sorbent pouch. In any embodiment of the first or second aspect of the invention, the sorbent pouch portion of the dialysis connector can be a separate structure that itself connects to the sorbent pouch. This enables a sorbent assembly that does not need a specific first and last sorbent pouch. In any embodiment of the first or second aspect of the invention, the dialysis machine connectors can be the same connectors that connect one sorbent pouch to another sorbent pouch. The dialysis machine connector, in any embodiment of the first or second aspect of the invention, could then connect to any sorbent pouch in the sorbent assembly. In any embodiment of the first or second aspect of the invention, a sorbent cartridge can contain any one of the sorbent pouches described herein. The sorbent cartridge can be constructed from any suitable material for use in a dialysis system and can have one or more compartments adapted for use by the sorbent pouches of the present invention. In any embodiment of the first or second aspect of the invention, a sorbent cartridge can also be comprised of a system of two or more modules that are adapted for use by the sorbent pouches as described in the sorbent assembly of the present invention. The modules can be connected together to form the sorbent cartridge wherein the two or more modules once formed can be connected to a dialysis flow path at the dialysate inlet end and at an outlet end.

The dialysate regeneration profile can be based on several parameters specific to the patient and/or to the dialysis session. For example, patient parameters can include, but are not limited to, patient BUN level, the amount of one or more other compounds in the patient's blood, patient weight, and past dialysis for the patient. Any of these patient parameters can be obtained via clinical assessments and tools known to those of ordinary skill. Dialysis parameters relate to dialysis session variables, and can include, but are not limited to, the dialysate circulation rate, the expected length of the dialysis session, the expected amount of any infusates added to the dialysate during dialysis, or the concentration of impurities in the water used to create the dialysate. When viewed as a whole, the collection of dialysis parameters can be used to create a dialysis prescription detailing the specific values for the dialysis session variables to be used for a particular patient.

Figure 4:
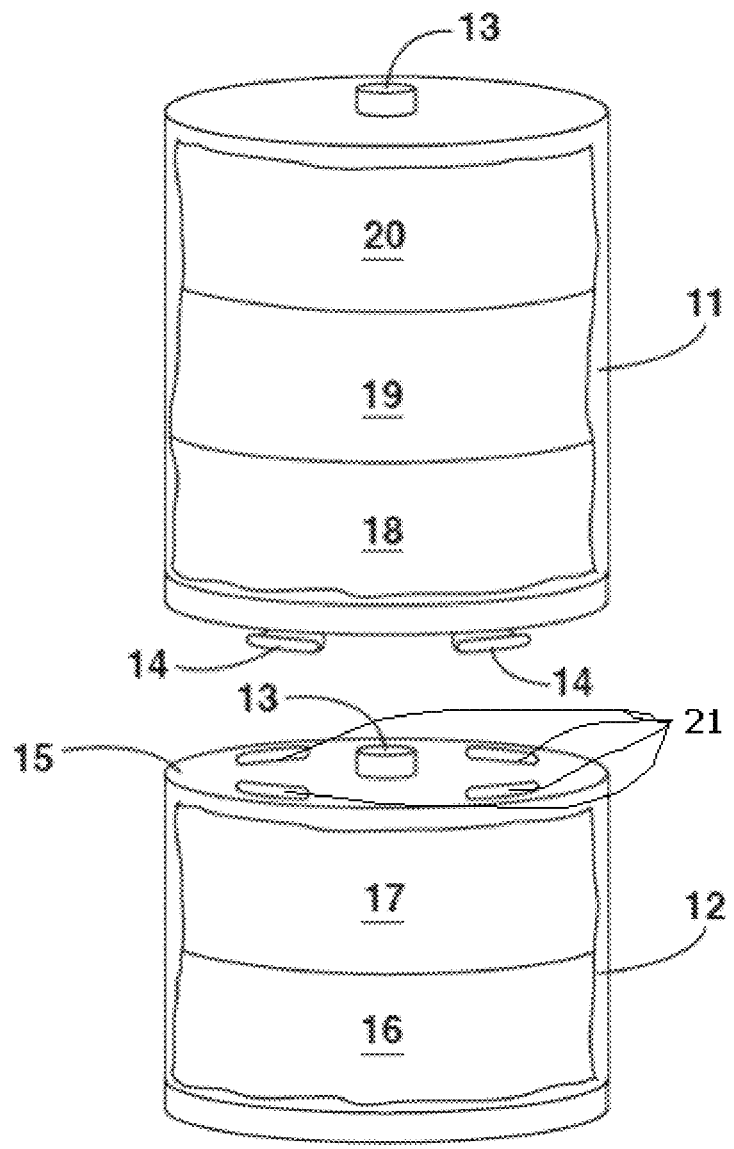
FIG. 4 is a cross-sectional view of a two-module sorbent cartridge with each module containing multiple stacked sorbent compartments.

In any embodiment of the first or second aspect of the invention, separate modules can be used to make up the sorbent cartridge with sorbent pouches within each module. A unitary structure, without an external housing, can be created by attaching modules together with connectors, wherein the fluid must pass through the connectors to move from one module to another module, as illustrated in FIG. 4. Module 12 can attach to module 11 in any embodiment of the first or second aspect of the invention, so that there is a seal between the modules. Fluid can pass from module 12, through connector 13 and into module 11. No external housing is necessary to create a sorbent cartridge in any embodiment of the first or second aspect of the invention. The modules 11 and 12 can be connected by mating latches 14 on module 11 with engagement members 21 disposed on the annular ring 15 on module 12 in the same manner as explained for connecting two sorbent pouches together. As explained above, modules of different sizes can be used to create a customizable dialysate regeneration system, wherein each module is itself a sorbent compartment, or can contain one or more sorbent compartments. In any embodiment of the first or second aspect of the invention, multiple modules containing the same sorbent material may be attached together in order to provide a larger amount of the particular sorbent material in a dialysate regeneration system. In any embodiment of the first or second aspect of the invention, each module can contain a different sorbent material. Module 12 can, for example, contain a sorbent pouch containing activated carbon 16 and a sorbent pouch containing hydrous zirconium oxide 17. Module 11 can contain a sorbent pouch containing ion-exchange resin 18, a sorbent pouch containing alumina and urease 19 and a sorbent pouch containing zirconium phosphate 20. The actual order of the sorbent pouches is flexible, and they may be placed in any order, so long as a zirconium phosphate sorbent pouch utilized is located downstream of a urease sorbent pouch.

Figure 5:
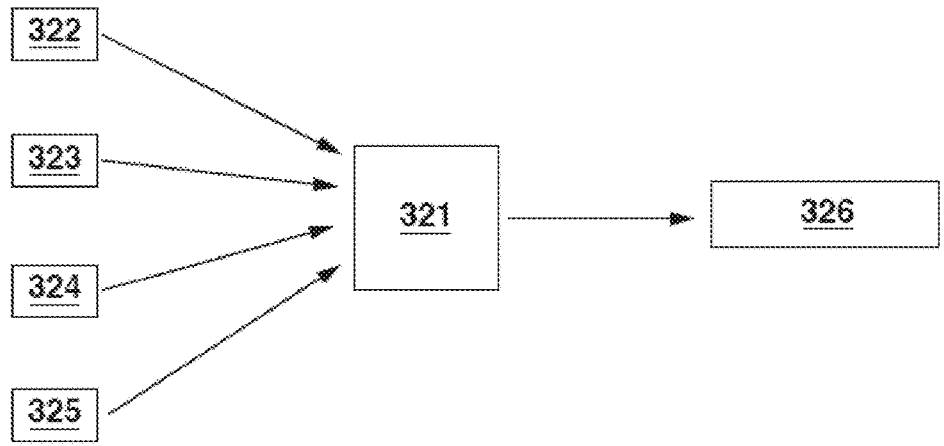
FIG. 5 is a flow diagram showing a control system for determining the correct amount of each sorbent material necessary for a dialysis session.

In any embodiment of the first or second aspect of the invention, a central processor can be utilized to determine the correct size or number of each of the sorbent compartments. The processor can determine the correct amount of each sorbent material needed based upon one or more patient and/or dialysis parameters. An example of a processing system for determining the correct amount of sorbent material for a patient is shown in FIG. 5. For example, the patient weight 322 may be entered into the central processor 321. The results of blood tests 323, such as the uremic state of the patient, may also be added to the central processor 321. Dialysis parameters 324, such as the expected length of the dialysis session, can be entered. Finally, previous dialysis results 325, such as the amount of the sorbent material used in a previous session and whether that amount was sufficient, can be included. The central processor 321 can then determine, based on all of the factors entered by the patient or health care professional, the most likely amount of each of the sorbent materials needed for the dialysis session. The central processor 321 can then display the amount of each material suggested for the session 326, and the patient or health care professional can select the proper size of the sorbent compartments, or proper number of sorbent compartments, for the given amount of material. In this way, the patient can receive a dialysate regeneration package that is customized to the patient's individual needs, reducing waste and costs. In any embodiment of the first or second aspect of the invention, the central processor can obtain patient information from other sources, such as the patient's electronic health records.

By way of one possible example, a user of the system can determine the BUN level of a patient who is about to undergo dialysis. If the patient's BUN level is higher than the average dialysis patient, a higher amount of zirconium phosphate may be required. The user may also determine the amount of creatinine in the patient's blood. If the patient's creatinine level is higher than the average dialysis patient, a higher amount of activated carbon may be required. The user may determine the level of certain ions, such as potassium, calcium or magnesium, in the patient's blood. If the levels of any of these ions are higher than the average dialysis patient, a higher amount of zirconium phosphate or ion-exchange resin may be required. The user may determine the phosphate levels in the patient's blood. If the phosphate level is higher than the average dialysis patient, a higher amount of hydrous zirconium oxide may be required. The user may enter the patient's weight; larger patients generally may have a greater amount of contaminants in their blood. If the patient's weight is higher than the average dialysis patient, a higher amount of each of the sorbent materials may be needed. The user can determine the expected length of the dialysis session. For longer sessions, higher amounts of each of the sorbent materials may be required. The user can enter the expected amount of infusates, such as calcium, magnesium or potassium that will be added to the dialysate during the dialysis session. Because these ions can be removed by zirconium phosphate or ion-exchange resin, adding infusates to the dialysate will result in a need for a higher amount of zirconium phosphate or ion-exchange resin. The level of impurities in the source water used during the dialysis session can also be determined. The source water may contain high levels of impurities that can be removed by the sorbent materials. This can include calcium, magnesium, potassium, or other ionic or non-ionic species that are removable by a sorbent material. For example, if the source water contains a high level of calcium, more zirconium phosphate may be required during the dialysis session. After all of the information has been entered by the user, the system can create a dialysate regeneration profile, determining the necessary amounts of zirconium phosphate, zirconium oxide, urease, activated carbon and ion-exchange resin required for the dialysis session. One or more of any of the patient parameters can be used to create the dialysate regeneration profile. The user can then select the proper sizes and amounts of each sorbent compartment.

Figure 6:
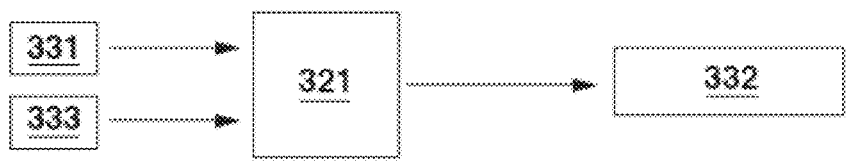
FIG. 6 is a flow diagram showing a learning module for a processor to update the correct amount of each sorbent material.

In any embodiment of the first or second aspect of the invention, the central processor 321 can learn the optimal amount of each sorbent material necessary given a set of patient parameters, as shown in FIG. 6. At the end of each session, the patient or health care professional can input into the central processor 321 whether the amount of each sorbent material was sufficient 331. Whether the amount was sufficient can be obtained from multiple sources. For example, if ammonia breakthrough occurs, then it is likely that the amount of zirconium phosphate used was not sufficient. If the concentration of phosphates in the patient's blood after the session remains high, then it is possible that there was not enough hydrous zirconium oxide used in the dialysate regeneration system. The central processor 321 can use that information to update internal tables 332. For example, if given a particular patient weight and uremic content, the central processor 321 initially determined a necessary amount of zirconium phosphate to use, and the results show that more zirconium phosphate was necessary, the central processor 321 can be updated so that the next time a patient has a similar weight and uremic content, the central processor 321 will determine a higher amount of zirconium phosphate to be used. In any embodiment of the first or second aspect of the invention, the remaining capacity of any of the sorbent compartments can be determined after a dialysis session. The remaining capacity 333 can then be entered into the central processor 321 and the internal tables 332 can be updated accordingly.

In any embodiment of the first or second aspect of the invention, no central processor need be used. Instead, a local database or table can be used. The database or table can contain information regarding the necessary amount of each sorbent material that corresponds to a variety of patient parameters.

In any embodiment of the first or second aspect of the invention, the sorbent compartments of the present invention can be individual sorbent modules that can connect to form a modular sorbent cartridge. Modular sorbent cartridges, wherein each module contains select sorbent materials, can be useful in sorbent dialysis. This modular design critically allows for certain portions of the sorbent cartridge to be discarded, refilled, recycled or recharged. In any embodiment of the first or second aspect of the invention, the sorbent materials can be structured into layers and/or intermixed. In particular, the modules can have the sorbent materials either intermixed or in layers wherein any combination of intermixed and layered modules can be used interchangeably together.

To save costs and waste, the modules of the modular sorbent cartridge may be rechargeable. The sorbent cartridges can be reusable or non-reusable, unless specifically specified as reusable. The sorbent material within the module can be recharged and made reusable by passing a solution containing the proper solutes through the layers of the sorbent module.

In any embodiment of the first or second aspect of the invention, the sorbent cartridge may be a permanent, fixed structure on a dialysis machine. The structure can be an empty chamber. The chamber may be large enough to hold enough of the individual sorbent compartments for even the most uremic patients. For patients that are less uremic, or need less of any particular sorbent material, filler compartments may be used to take up the empty space in the chamber. The filler compartments may be filled with any inert material that will still allow fluid to flow through the compartments, including but not limited to sand or glass beads. In any embodiment of the first or second aspect of the invention, the filler compartments can be modules designed to port fluid, such as with internal tubing.

In any embodiment of the first or second aspect of the invention, the sorbent compartments can be separate sorbent pouches that contain individual portions of sorbent material, or alternatively contain multiple layers of sorbent material. The sorbent pouches are designed such that spent dialysate or water may pass through the sorbent pouch and into the sorbent material or materials within, and the spent dialysate or water may then pass out of the sorbent pouch, while the sorbent materials remain inside the sorbent pouch. In any embodiment of the first or second aspect of the invention, a compartment can comprise multiple sorbent pouches. In any embodiment of the first or second aspect of the invention, each sorbent pouch can constitute a sorbent compartment.

Figure 7:
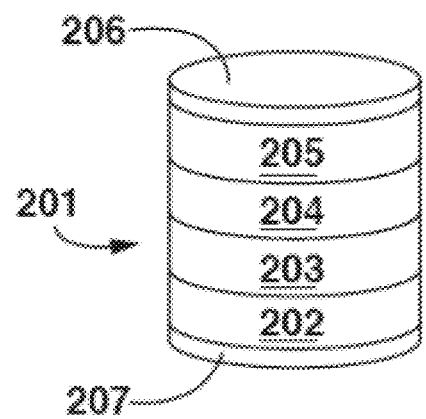
FIG. 7 is a perspective view of a sorbent cartridge comprising sorbent compartments containing activated carbon, hydrous zirconium oxide, urease, alumina, and zirconium phosphate.

One non-limiting embodiment of the first or second aspect of the invention is shown in FIG. 7. The sorbent cartridge 201 can comprise a sorbent pouch containing activated carbon 202, a sorbent pouch containing hydrous zirconium oxide 203, a sorbent pouch containing alumina and urease 204, and a sorbent pouch containing zirconium phosphate 205. In any embodiment of the first or second aspect of the invention, alumina can be contained in one sorbent pouch and urease in another sorbent pouch. Spent dialysate can enter through the bottom surface 207 of the sorbent cartridge 201, and flow through each of the sorbent pouches sequentially, and then flow out of the sorbent cartridge 201 through the top surface 206 of the sorbent cartridge 201. In this way, the spent dialysate can come into contact with each sorbent material layer in series, while each sorbent material layer is kept separate from each of the other layers. One skilled in the art will understand that the sorbent pouches may be arranged in alternate orders and still be within the scope of the invention. For example, the first sorbent pouch 202 may contain activated carbon, the second sorbent pouch 203 may contain alumina and urease, the third sorbent pouch 204 may contain hydrous zirconium oxide, and the fourth sorbent pouch 205 may contain zirconium phosphate. In any embodiment of the first or second aspect of the invention, the first sorbent pouch 202 may contain activated carbon, the second sorbent pouch 203 may contain alumina and urease, the third sorbent pouch 204 may contain zirconium phosphate and the fourth sorbent pouch 205 may contain hydrous zirconium oxide. The precise order of the sorbent pouches within the sorbent cartridge is flexible, so long as a sorbent pouch containing zirconium phosphate is located downstream of a sorbent pouch containing urease. In any embodiment of the first or second aspect of the invention, a sorbent pouch can contain multiple sorbent materials, either arranged in layers or alternatively intermixed within the sorbent pouch. Additionally, any number of sorbent pouches arranged sequentially in the sorbent cartridge is envisioned.

The sorbent pouches of the first or second aspect of the invention can be constructed in any shape. For convenience, they are often drawn as circular or disc shaped. However, any of the described embodiments of the first or second aspects of the invention can be made in any shape, including triangular, rectangular, etc.

Figure 8:
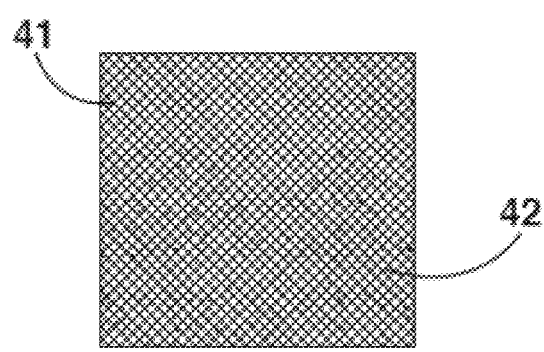
FIG. 8 shows a top view of a rectangular sorbent pouch.
Figure 9:
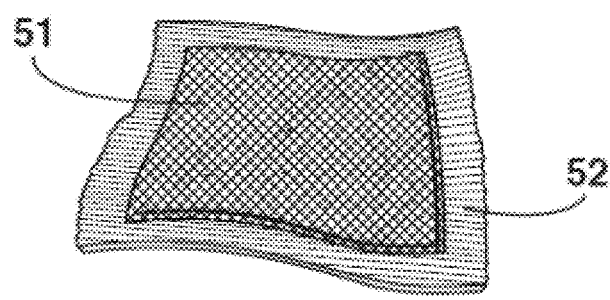
FIG. 9 shows a perspective view of a rectangular sorbent pouch.
Figure 10:
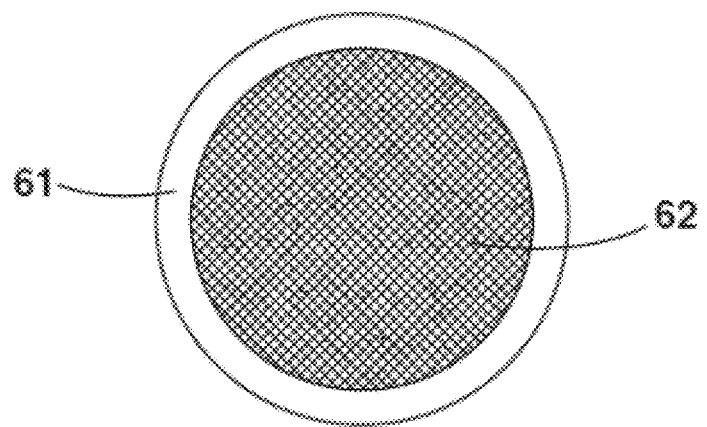
FIG. 10 shows top view of a disc-shaped sorbent pouch.
Figure 11A:
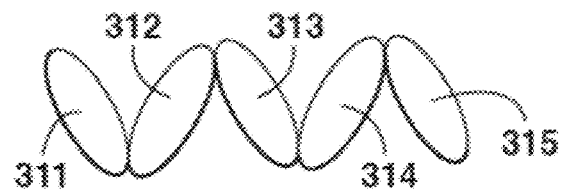
FIG. 11a is a side view of a string of disc-shaped sorbent pouches.
Figure 11B:
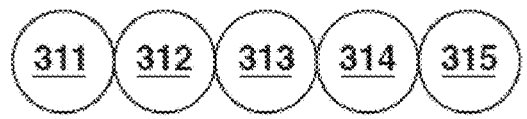
FIG. 11b is a top view of a string of disc-shaped sorbent pouches.
Figure 11C:
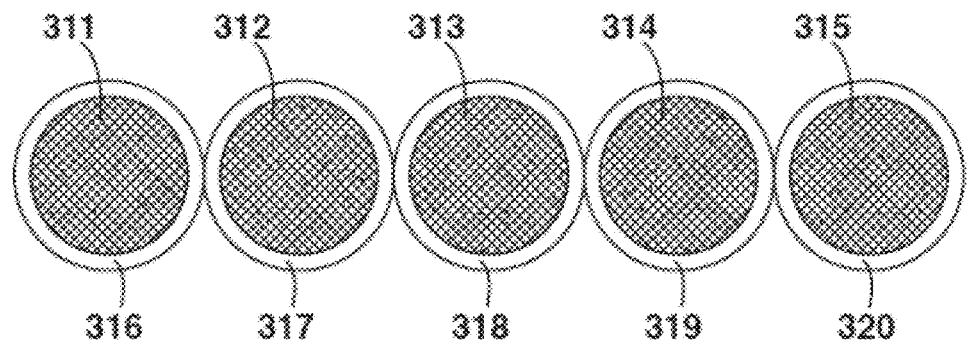
FIG. 11c is a top view of a string of disc-shaped sorbent pouches that are connected by their outer edges.
Figure 11D:
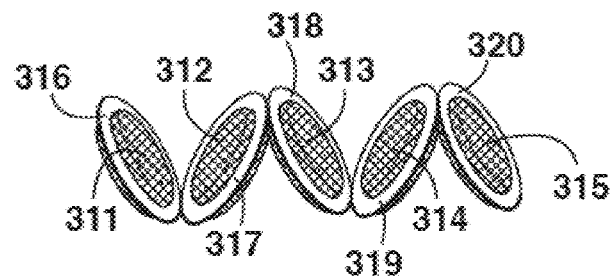
FIG. 11d is a perspective view of a string of disc-shaped sorbent pouches that are connected by their outer edges.
Figure 12A:
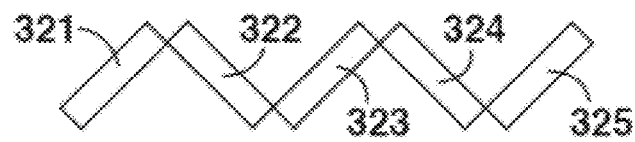
FIG. 12a is a side view of a string of rectangular sorbent pouches.
Figure 12B:
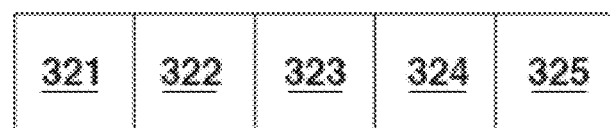
FIG. 12b is a top view of a string of rectangular sorbent pouches.
Figure 12C:
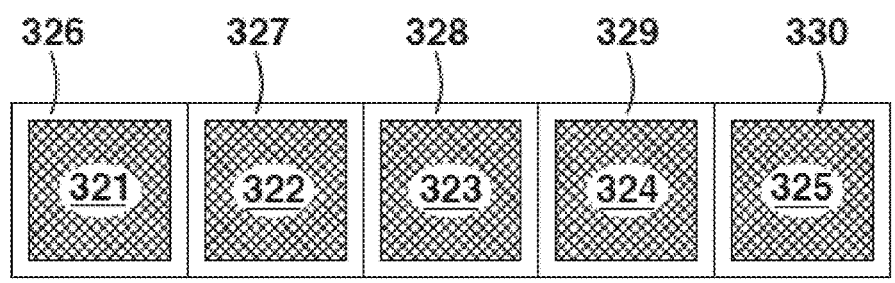
FIG. 12c is a top view of a string of rectangular sorbent pouches connected by their outer edges.

For example, FIG. 8 shows a top view of a rectangular pouch, whereas FIG. 9 shows a perspective view of a rectangular shaped pouch, and FIG. 10 shows a disc-shaped pouch. The sorbent pouches may be constructed of any known material, including ashless filter paper, bolting cloth, nylon, porous polymer and porous metal, Dacron and polyethylene terephthalate as described herein, and each can be constructed in any shape.

In any embodiment of the first or second aspect of the invention, the sorbent pouches of the invention can be configured as shown in FIG. 8. The sorbent pouch 41 can be constructed of a material that can allow fluid to pass through the sorbent pouch 41, but will not allow the sorbent material 42 contained within the sorbent pouch to pass out of the sorbent pouch 41. The sorbent material 42 can be placed loosely within the sorbent pouch 41, allowing the sorbent material 42 to move within the sorbent pouch 41, but not to travel out of the sorbent pouch 41. The sorbent pouch 41 can be made in any size or shape. In any embodiment of the first or second aspect of the invention, as shown in FIG. 9, the sorbent pouch 51 can be roughly rectangular shaped. In any embodiment of the first or second aspect of the invention, as shown in FIG. 10, the sorbent pouch 61 can be disc-shaped. In any embodiment of the first or second aspect of the invention, the sorbent pouch can be shaped to be adapted into an internal cavity defined by a sorbent cartridge. In this way, the sorbent pouch may fit in the space, such that there may be void space, but such that the sorbent pouch generally fits the space. For example, a sorbent cartridge having a cylindrical internal cavity can accommodate a circular or disc-shaped sorbent pouch, while a sorbent cartridge having a conical internal cavity could accommodate a triangular sorbent pouch, and a sorbent cartridge having a square or rectangular internal cavity could accommodate a square or rectangular-shaped sorbent pouch.

FIG. 9 shows a rectangular sorbent pouch in which the sorbent material is contained in a raised inner portion of the sorbent pouch 51, while the outer perimeter of the sorbent pouch, having a serrated edge 52, is sealed by any means known in the art, including heat or pressure stamping, sewing, or adhesive sealing. The outer serrated edge 52 of the sorbent pouch may be permanently sealed, or may alternatively be resealable, such that the sorbent pouch may be opened and reclosed. For example, the serrated edge 52 may be sealed with a resealable adhesive, hook and loop fasteners (not shown), or with interlocking ridges (not shown) that may be separated and reclosed by the user. Optionally, a latch member (not shown) may be included on the serrated edge 52 of the sorbent pouch to provide additional strength in sealing the sorbent pouch. In any embodiment of the first or second aspect of the invention, the outer edge may simply be a folded edge. In use, compression from the other materials within a sorbent cartridge can keep the folded edge sealed and the sorbent materials inside the sorbent pouch. In any embodiment of the first or second aspect of the invention, the sorbent pouch may be sealed with drawstrings that when tightened create a seal.

In any embodiment of the first or second aspect of the invention, the sorbent pouches can be formed from a porous material that allows fluid to pass through the sorbent pouches wherein substantially all of the sorbent material or particles are retained by the porous material. Sorbent materials are generally formed from a solid substance that adsorbs and/or absorbs to other substances. In any embodiment of the first or second aspect of the invention, the porous material can allow fluid to pass through the sorbent pouches but substantially retains the sorbent material in the sorbent pouch. In any embodiment of the first or second aspect of the invention, the porous material can allow fluid to pass through the sorbent pouches but retain at least 98% by weight of one sorbent material in the sorbent pouch. In any embodiment of the first or second aspect of the invention, the porous material can allow fluid to pass through the sorbent pouches but can retain anywhere from at least 70%, 75%, 80%, 85%, 90%, 92%, 93%, 94%, 95%, 96%, or 97% by weight of one sorbent material in the sorbent pouch.

In any embodiment of the first or second aspect of the invention, the pore size of one or more of the sorbent pouches may be large enough so that the sorbent material can leave the sorbent pouch. For example, a sorbent pouch containing urease may be made with a pore size large enough to allow the urease to travel through the sorbent pouch. The urease in any embodiment of the first or second aspect of the invention, can be dissolved by the fluid as it passes through the sorbent pouch during priming of the sorbent cartridge prior to dialysis, and the urease can exit the sorbent pouch. The urease in solution can then contact a sorbent pouch containing immobilized alumina, where the urease will become bound to the alumina in the alumina sorbent pouch.

The size of the sorbent pouches is flexible. Because different amounts of each sorbent material may be required for a dialysis session, the sorbent pouches of the present invention may be in multiple sizes. In any sorbent pouch, glass beads can be incorporated into the sorbent material to facilitate flow.

The sorbent pouches may be constructed of a flexible or rigid material. The flexible material can be selected from any non-toxic material suitable for the intended use in a dialysis wherein the material can allow fluid to pass through the material yet substantially retains the sorbent material in the sorbent pouch. The flexible material can be selected from materials that have the appropriate porosity, strength and durability. In any embodiment of the first or second aspect of the invention, the flexible material can allow fluid to pass through the sorbent pouches but can retain at least 98% by weight of one sorbent material in the sorbent pouch. In any embodiment of the first or second aspect of the invention, the flexible material can allow fluid to pass through the sorbent pouches but can retain anywhere from at least 70%, 75%, 80%, 85%, 90%, 92%, 93%, 94%, 95%, 96%, or 97% by weight of one sorbent material in the sorbent pouch. When the material is selected for use with urease, alumina may also be provided in the sorbent pouch. Because the alumina will adsorb the urease, and keep the urease from flowing out of the sorbent pouch, the flexible material need only substantially retain the alumina.

In any embodiment of the first or second aspect of the invention, the sorbent pouches may be constructed out of both a flexible and a rigid material. For example, the top and bottom of the sorbent pouch may be constructed from a flexible material, while the sides of the sorbent pouch may be constructed from a rigid material. In any embodiment of the first or second aspect of the invention, the sorbent pouches can be constructed of a material such as a porous polymer. The polymer may be made porous by creating small holes or pores in an otherwise solid polymer material. The polymer may be constructed from polyethylene terephthalate, high density polyethylene, low density polyethylene, polyvinyl chloride, polypropylene, polystyrene, or any other polymer known in the art. In any embodiment of the first or second aspect of the invention where the sorbent pouch is made of fabric, the weave of the fabric can have a specified porosity suitable for use of the sorbent material described herein for the intended use of dialysis. The pores of the sorbent pouch material must be large enough to allow the spent dialysate to freely travel into and out of the sorbent pouch, while at the same time must be small enough to keep the particles of the sorbent material inside the sorbent pouch. For this reason, sorbent pouches with different pore or mesh sizes can be utilized for different material layers. In any embodiment of the first or second aspect of the invention, the sorbent pouch may be made out of a natural fiber, such as cotton. In any embodiment of the first or second aspect of the invention, the sorbent pouch may be constructed from ashless filter paper. The sorbent pouches may also be constructed out of a synthetic material such as Dacron, or polyethylene terephthalate.

In any embodiment of the first or second aspect of the invention, multiple sorbent pouches may be connected as a string of sorbent pouches, as shown in FIGS. 11a, 11b, 11c, 11d, 12a, 12b and 12c. The individual sorbent pouches 311-315 in the case of disc shaped sorbent pouches and 321-325 in the case of rectangular sorbent pouches, may be permanently or separably connected at their outer edges by any means known in the art, including by perforations in the material forming the outer edges 316-320 in the case of disc shaped sorbent pouches and 326-330 in the case of rectangular sorbent pouches. The individual sorbent pouches comprising the string of sorbent pouches may be composed of the same material; may be composed of different materials such that each sorbent pouch in the string of sorbent pouches is composed of a different material; or may be composed of different materials such that some sorbent pouches in the string of sorbent pouches are composed of the same material, while others are composed of differing materials, and are arranged in a random or repeating pattern. The materials of which the individual sorbent pouches are composed may be selected with particularity to the sorbent material housed inside the sorbent pouch. For example, sorbent pouches containing activated carbon may require a larger mesh to prevent the larger particles from escaping the sorbent pouch. By contrast, sorbent pouches containing hydrous zirconium oxide may require a smaller mesh to prevent the smaller particles from escaping the sorbent pouch. Any combination of sorbent pouch materials and mesh sizes among the string of sorbent pouches, and any number of individual sorbent pouches making up the string of sorbent pouches, is envisioned. Additionally, the sorbent pouches may be constructed in any shape, including but not limited to, rectangular or circular.

Figure 13A:
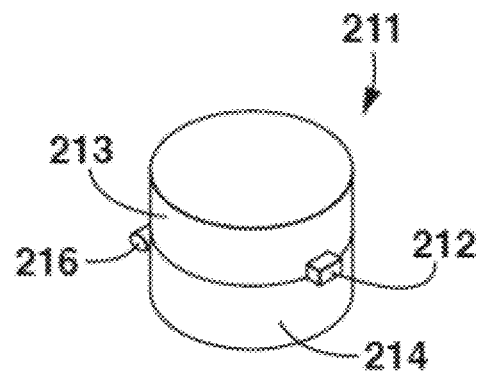
FIG. 13a is a perspective view of a sorbent pouch having the ability to open.
Figure 13B:
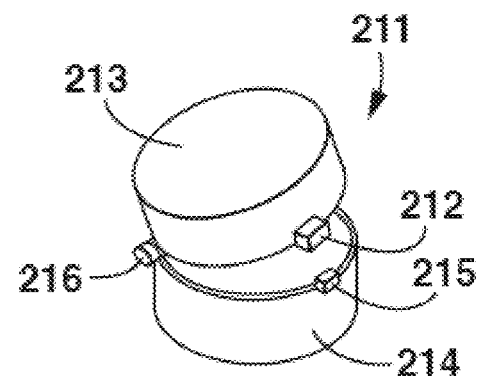
FIG. 13b is a perspective view of a sorbent pouch in an open state.

In any embodiment of the first or second aspect of the invention, the sorbent pouches of the present invention may be designed so that they can be opened, as shown in FIG. 13*a*. Top portion 213 of the sorbent pouch 211 and bottom portion 214 of the sorbent pouch 211 may be connected by a hinge 216 and a latch member 212. When latch member 212 on the top portion 213 of sorbent pouch 211 is engaged with a flange 215 (shown in FIG. 13*b*) on bottom portion 214 of the sorbent pouch 211, the top portion 213 of the sorbent pouch 211 can be firmly sealed to the bottom portion 214 of the sorbent pouch 211. As shown in FIG. 13*b*, when latch member 212 of the sorbent pouch 211 is disengaged from flange 215, top portion 213 can pivot on hinge 216 to separate from the bottom portion 214 of the sorbent pouch 211. The sorbent material (not shown) within the sorbent pouch 211 can then be removed in order to be discarded or recharged. The sorbent pouch 211 itself may be reused. The sorbent pouch 211 can be closed as shown in FIG. 13*b* by pivoting the top portion 213 of the sorbent pouch 211 so that top portion 213 and bottom portion 214 meet, and reengaging latch member 212 on the top portion 213 of the sorbent pouch 211 with flange 215 on the bottom portion 214 of the sorbent pouch 211. Any type of connection between the top portion and bottom portion of the sorbent pouch is contemplated by this invention. For example, the top portion of the sorbent pouch may include multiple latches in the absence of a hinge member, while the bottom portion of the sorbent pouch can include engagement members. When the top portion is placed onto the bottom portion and twisted, the latches can engage the engagement members, creating a connection that can be resistant to inadvertent opening. In order for the connection to be broken, the top portion of the sorbent pouch can be twisted in the opposite direction, allowing the two portions to separate.

In any embodiment of the first or second aspect of the invention, the sorbent pouches may be constructed so that they cannot easily be opened. In any embodiment of the first or second aspect of the invention, the sorbent pouches can be completely sealed to form a complete enclosure around the sorbent material. During construction of the sorbent pouch, once the sorbent material is added, the sorbent pouch can be sealed by any possible means. For example, the sorbent pouches can be heat sealed to fuse the edges of the sorbent pouch together. In any embodiment of the first or second aspect of the invention, an adhesive may be used to connect the edges together. In any embodiment of the first or second aspect of the invention where a fiber is used to construct the sorbent pouches, the edges may be sewn or woven together to create a sealed sorbent pouch. Any type of chemical or mechanical closure to form the sorbent pouches is contemplated by this invention.

Figure 14A:
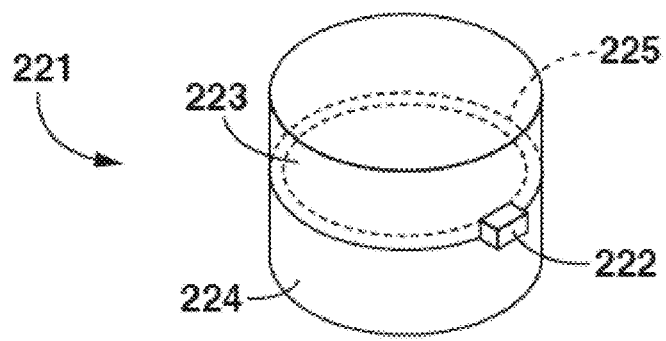
FIG. 14a is a perspective view of a sorbent pouch having an internal sealing member.
Figure 14B:
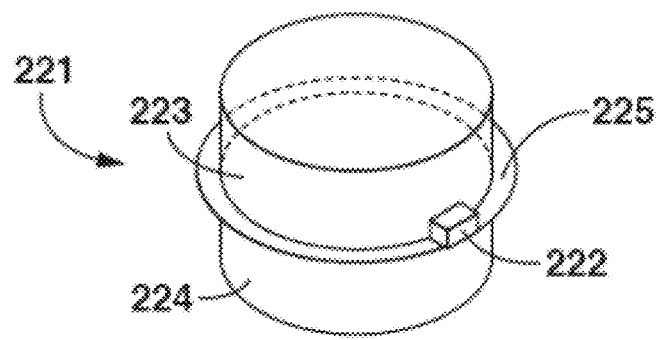
FIG. 14b is a perspective view of a sorbent pouch having an external sealing member.

In any embodiment of the first or second aspect of the invention, as shown in FIGS. 14*a* and 14*b*, the sorbent pouches may have an interior or exterior ring 225 disposed inside of or around the sorbent pouch 221, respectively, creating an additional sealing member to secure the top portion 223 of the sorbent pouch 221 to the bottom portion 224 of the sorbent pouch 221. The coupled surfaces of the rings may be coated in an adhesive material, or the rings may be attached by any other known coupling means. In any embodiment of the first or second aspect of the invention, the rings may be welded. In any embodiment of the first or second aspect of the invention, the rings may be mechanically attached to the sorbent pouches such as with rivets, screws or clamps. In any embodiment of the first or second aspect of the invention, engagement hooks may be placed on the rings, wherein the engagement hooks can attach to the sorbent pouch in a similar fashion as described for connecting the top and bottom portions of the sorbent pouches as shown in FIGS. 13*a* and 13*b*.

Figure 15:
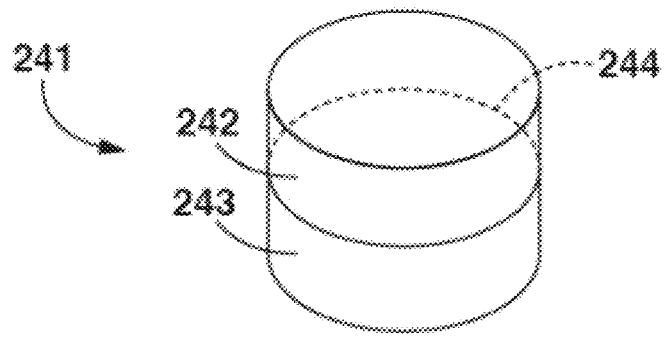
FIG. 15 is a perspective view of a sorbent pouch with an internal separator.

In any embodiment of the first or second aspect of the invention, such as that shown in FIG. 15, a single sorbent pouch can contain multiple sorbent materials. Sorbent pouch 241 can comprise a separator 244 positioned within the sorbent pouch. The separator 244 can run through the entire interior space of the sorbent pouch 241. The separator 244 creates, within the sorbent pouch 241, a top portion 242 and a bottom portion 243, which are kept completely separate from each other. One sorbent material may be placed in the top portion of the sorbent pouch 242, and a different sorbent material may be placed in the bottom portion of the sorbent pouch 243. This allows two different materials to be placed within a single sorbent pouch 241, but remain separate from one another. In any embodiment of the first or second aspect of the invention, two or more sorbent materials can be placed in a single sorbent pouch without a separator. The sorbent materials may be arranged in layers within the sorbent pouch, or may be intermixed. The separator 244 can be constructed from the same material as the pouch itself, or may be a different material that still allows fluid to pass through the separator freely while preventing passage of the sorbent material.

In any embodiment of the first or second aspect of the invention, more than one separator can be used within a single sorbent pouch. The first or second aspect of the invention contemplate sorbent pouches containing 2, 3, 4 or more separators within a single sorbent pouch.

In any embodiment of the first or second aspect of the invention, multiple sorbent materials can be mixed within a sorbent pouch. Mixing different sorbent materials together can be accomplished without a loss in efficiency of the sorbent materials.

Figure 16:
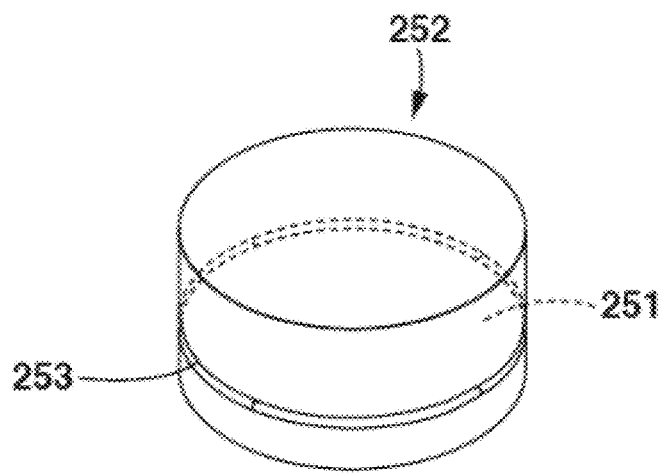
FIG. 16 is a perspective view of a sorbent cartridge and sorbent pouch with an o-ring seal member.

The sorbent pouches of the first or second aspect of the invention can have a mechanism to create a seal between the sorbent pouch and the inner surface of the sorbent cartridge in which the sorbent pouch is placed, such that fluid is kept from flowing around the sorbent pouch and instead is directed into the sorbent pouch. FIG. 16 shows a non-limiting embodiment of a seal mechanism of the first or second aspect of the invention. A flexible sorbent pouch 251, such as one made out of a fiber, can be placed inside of a sorbent cartridge 252. In any embodiment of the first or second aspect of the invention, the sorbent pouch may be made out of a rigid material, such as a polymer or metal. In order to avoid a situation in which spent dialysate flows around the sorbent pouch and therefore does not contact the sorbent material inside the sorbent pouch, the sorbent pouch 251 may be sealed to the sorbent cartridge 252. O-ring 253 placed on the circumference of sorbent pouch 251 can form a seal with the sorbent cartridge 252 so as to prevent spent dialysate from flowing around the sorbent pouch 251, and instead directing the dialysate through the sorbent pouch 251. The sorbent pouch 251 may be sized so that the circumference of the sorbent pouch 251 is slightly wider than that of the sorbent cartridge 252. This will ensure that the sorbent pouch 251 covers the entire inner area of the sorbent cartridge 252 and that there are no spaces for fluid to pass by without flowing through the sorbent pouch 251. O-ring 253 can also serve to ensure that sorbent pouch 251 keeps the intended shape by providing a semi-rigid border.

Figure 17:
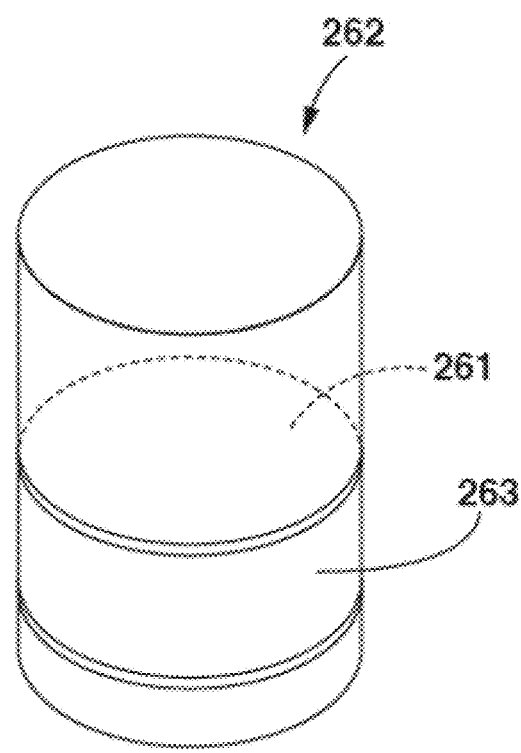
FIG. 17 is a perspective view of a sorbent pouch with an elastomeric material on the side walls.

In any embodiment of the first or second aspect of the invention, as shown in FIG. 17, an elastomeric material 263 may be disposed on the edges of the sorbent pouch 261. When the sorbent pouch 261 is placed in the sorbent cartridge 262, the elastomeric material 263 functions like the o-ring described above to create a seal and keep liquid from flowing around the sorbent pouch 261. The elastomeric material 263 can be made to completely cover the outside edges of the sorbent pouch 261, or the elastomeric material can be disposed in one or more thin strips of material. In any embodiment of the first or second aspect of the invention, the inside walls of the sorbent cartridge may be coated in an elastomeric substance, which will function to form the same seal when a rigid or semi-rigid sorbent pouch is placed within. In any embodiment of the first or second aspect of the invention, the sorbent pouches may be constructed to be slightly larger than the sorbent cartridge. When the user inserts the sorbent pouches into the sorbent cartridge, the sorbent pouches can be compressed slightly to fit in the sorbent cartridge. This will ensure that the sorbent pouches cover the entire area inside the sorbent cartridge and facilitate the formation of a seal around the edges of the sorbent pouch.

Figure 18:
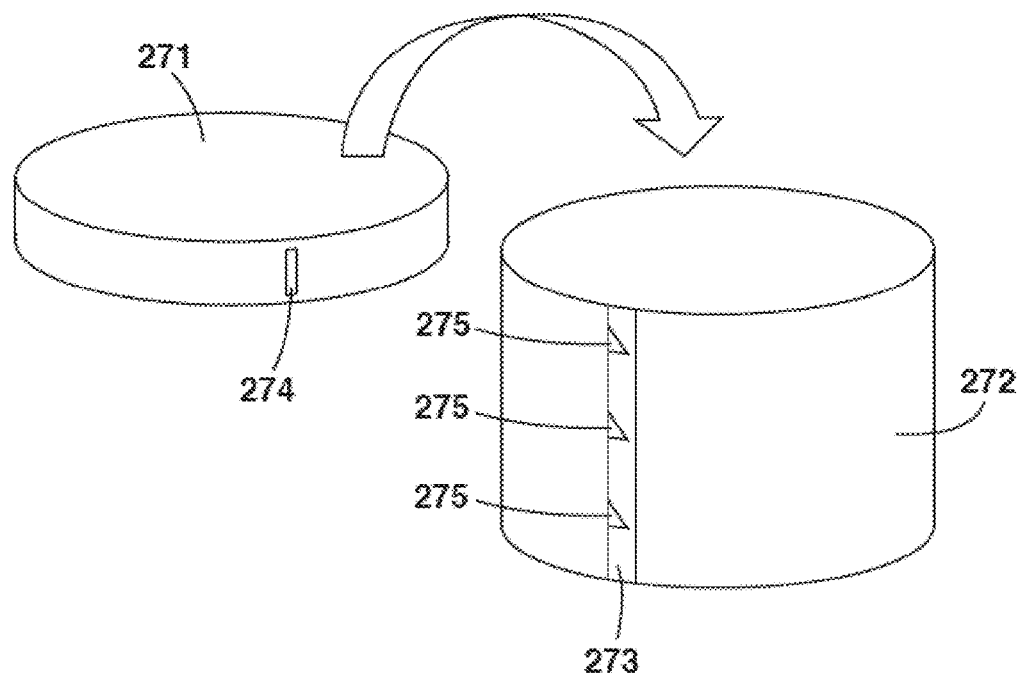
FIG. 18 is a perspective view of a sorbent pouch and a sorbent cartridge with a key function to ensure correct alignment.

In any embodiment of the first or second aspect of the invention, it may be important to ensure that the sorbent pouches are properly inserted into the sorbent cartridge. Any method of doing so is contemplated by the first or second aspect of the invention. One non-limiting example is shown in FIG. 18. Groove 273 may be created in the wall of the sorbent cartridge 272. A key 274, or flange, may be disposed on the side of the sorbent pouch 271. In order for the sorbent pouch 271 with key 274 to fit within the sorbent cartridge 272, the key 274 must be aligned with groove 273 in the sorbent cartridge 272 wall. This will ensure that the sorbent pouch 271 is disposed within the sorbent cartridge 272 with the correct alignment. In any embodiment of the first or second aspect of the invention, optional ridges 275 may be placed within groove 273. The ridges 275 can serve to lock the sorbent pouch 271 in place vertically within the sorbent cartridge 272. The ridges 275 may be designed so that they are angled on the top portion of the ridge and flat on the bottom portion of the ridge. Once the key 274 passes a ridge 275 in a downward direction, the ridge 275 can serve to keep the sorbent pouch 271 from inadvertently moving back upward within the sorbent cartridge 272.

The ridges 275 may be designed such that the sorbent pouch 271 may be removed upward only with the use of force greater than would be expected from inadvertent moving but not so much force as to prevent intentionally lifting the sorbent pouch out of the sorbent cartridge 272. This can be accomplished by using a semi-rigid material as either the key 274, the ridges 275, or both, such that when enough force is applied, the key 274 or ridges 275 can be bent far enough to allow removal of the sorbent pouch 271, after which the key 274 or ridges 275 can return to their original shape. In any embodiment of the first or second aspect of the invention, the ridges 275 may be attached with a spring mechanism that is connected to a button (not shown), such that when the button is depressed the ridges 275 recede into the interior wall of the sorbent cartridge 272 and allow easy removal of the sorbent pouch 271 from the sorbent cartridge 272.

In any embodiment of the first or second aspect of the invention, the sorbent pouches may be loosely contained within the sorbent cartridge. The sorbent pouches need not be made the same size as, or larger than, the sorbent cartridge. One or more sorbent pouches may be constructed of a smaller size than the interior circumference of the sorbent cartridge, and may be simply placed in the sorbent cartridge.

After construction of the sorbent pouch containing a sorbent material or materials, the material within the sorbent pouch can be washed so as to remove any particles smaller than the pore or mesh size of the sorbent pouch material. This will ensure that all particles within the sorbent pouch are large enough so that they cannot inadvertently pass out of the sorbent pouch. Thus, when used in a sorbent cartridge, the sorbent pouches themselves can act as a particulate filter, ensuring that no particulate matter of the sorbent material, or any other particulate matter, can pass downstream. This may eliminate the need for the use of external particulate filters.

In any embodiment of the first or second aspect of the invention, antimicrobial or antibacterial material may be impregnated into the sorbent pouch. This allows sterilization of the dialysate as the dialysate flows through the sorbent cartridge, and can eliminate the need for antimicrobial filters. In any embodiment of the first or second aspect of the invention, medication such as heparin or other anticoagulants, or antibiotics may be impregnated into the sorbent pouch. This can allow administration of these medications to the patient without the need for adding the drugs to the dialysate.

Figure 19:
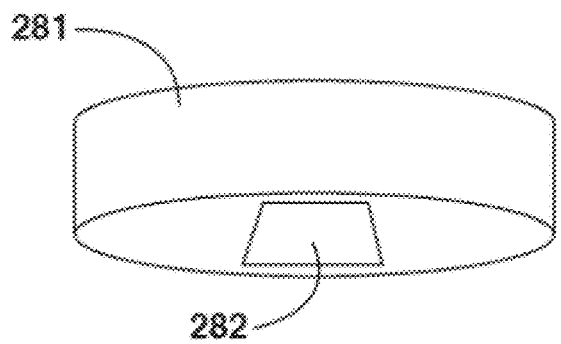
FIG. 19 is a perspective view of a sorbent pouch with a double layer of material in the center to control flow through the sorbent pouch.

In any embodiment of the first or second aspect of the invention, flow throughout the sorbent pouch can be controlled by variations in the sorbent pouch material. Generally, fluid moving through a conduit will move most quickly through the center of the conduit, and more slowly towards the edges. To ensure that fluid travels more evenly throughout the sorbent pouch, the sorbent pouch can be constructed such that more fluid enters the sorbent pouch on the outer edges of the sorbent pouch than enters in the center. One non-limiting example is shown in FIG. 19. A sorbent pouch 281, such as one made out of a fabric, can be constructed with an extra layer of fabric 282 in the center of the bottom portion of the sorbent pouch 281. This extra layer of fabric 282 effectively reduces the mesh size of the sorbent pouch 281 in that location. With a smaller mesh size, resistance to flow can be higher in the center of the sorbent pouch 281 and fluid flow can be more evenly distributed to the edges of the sorbent pouch 281. In any embodiment of the first or second aspect of the invention where the sorbent pouch is made out of metal or a polymer, the same effect can be created by making a smaller pore size, or alternatively less pores, in the center of the sorbent pouch. In any embodiment of the first or second aspect of the invention, a separator, similar to the one shown in FIG. 15 can be utilized in the middle of the sorbent pouch. The separator can be constructed as described above, such as with an extra layer of fabric near the center, to better control the flow of fluid throughout the sorbent pouch. Although shown in FIG. 19 as a centrally positioned rectangular layer, the extra layer of fabric 282 or other material may be positioned anywhere along the outer surface of the sorbent pouch 281, and may take any shape, such as circular, rectangular, triangular, etc.

In any embodiment of the first or second aspect of the invention, a patterned flow of fluid through the sorbent cartridge can be created. Occlusions, or blockages, of some of the pores can result in restricted flow through some portions of the sorbent pouch. In any embodiment of the first or second aspect of the invention, some of the pores in the sorbent pouch may be larger or smaller than other pores in the rest of the sorbent pouch. Flow will be increased through the larger pores as compared to the smaller pores, allowing control over fluid flow into and out of the sorbent pouch.

Fluid flows through sorbent materials of varying particle sizes and granular diameters at various rates and pressures. Fluid flows at a higher rate and at a lower pressure through granules of larger diameter, while fluid flows at a slower rate and at a higher pressure through granules of smaller diameter. Wicking can occur when fluid generally flows in the direction of areas of least pressure. For example, fluid flow through a fine particle sorbent material, such as zirconium phosphate, can result in wicking. In such an instance, the fluid has a tendency to flow towards an area of lower resistance, generally near the wall of the container. This can result in the fluid not flowing through a large portion of the sorbent material, such that the fluid is not coming into contact with the sorbent materials. To ensure that fluid flows through the sorbent pouch and the sorbent materials more evenly, the sorbent pouches of the present invention can be constructed such that fluid is directed to flow away from the walls of the sorbent pouch and towards the interior of the sorbent pouch.

Figure 22:
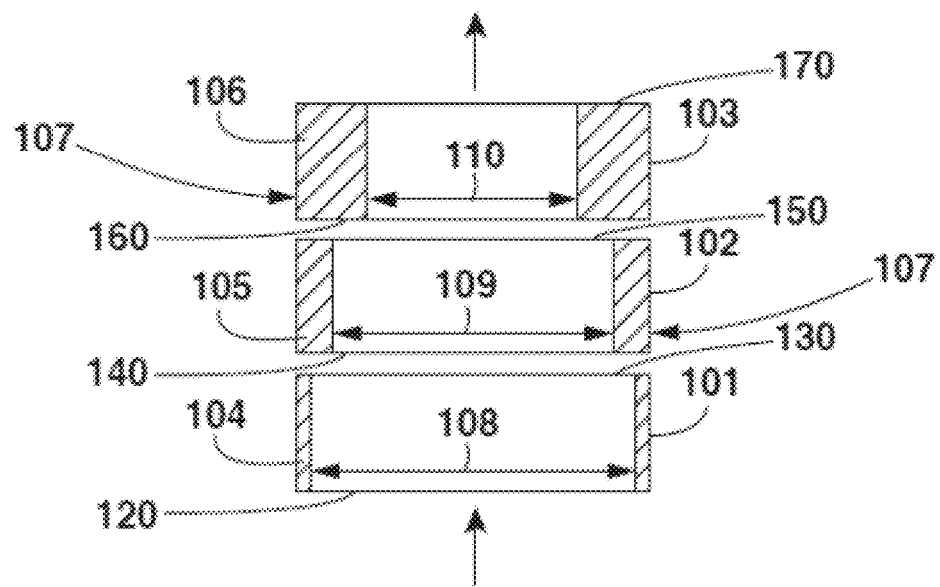
FIG. 22 shows an exploded cross-sectional view of a sorbent cartridge having stacked sorbent pouches, with each sorbent pouch in series having a thicker sidewall, and therefore smaller interior diameter, than that of the previous sorbent pouch in series.

In any embodiment of the first or second aspect of the invention, flow of fluid through the sorbent pouches can be controlled by varying the interior diameters of the sorbent pouches. In FIG. 22, the second sorbent pouch 102 has an interior wall 105 that is thicker than the interior wall 104 of the first sorbent pouch 101, such that the interior diameter 109 of the second sorbent pouch 102 is smaller than the interior diameter 108 of the first sorbent pouch 101. Similarly, the third sorbent pouch 103 has an interior wall 106 that is thicker than the interior wall 105 of the second sorbent pouch 102, such that the interior diameter 110 of the third sorbent pouch 103 is smaller than the interior diameter 109 of the second sorbent pouch 102. Each sorbent pouch can have a wall that is thicker than that of the immediately preceding sorbent pouch in a direction from the bottom surface 120 of the first sorbent pouch 101 to the top surface 170 of the third sorbent pouch 103 while maintaining a substantially identical outer diameter among each sorbent pouch. Any number of sorbent pouches can be used in any embodiment of the first or second aspect of the invention. Fluid flowing through the bottom surface 120 of the first sorbent pouch 101 to the top surface 130 of first sorbent pouch 101, through the bottom surface 140 and top surface 150 of the second sorbent pouch 102, and through the bottom surface 160 to the top surface 170 of the third sorbent pouch 103, is directed into the interior space of each pouch. Because each sorbent pouch has a thicker wall than the preceding sorbent pouch in series, each sorbent pouch has a smaller effective area through which fluid can flow than the preceding sorbent pouch. This gradually decreasing flow area will result in pushing the fluid moving from one sorbent pouch to another sorbent pouch along the edges of the sorbent pouches near the wall of the sorbent cartridge 107 towards the center of the subsequent sorbent pouch. In any embodiment of the first or second aspect of the invention, the wall of each sorbent pouch can be between 5-10% thicker than the wall of the preceding sorbent pouch. In any embodiment of the first or second aspect of the invention, the thickness of the wall of each sorbent pouch can be between 1-5%, 10-15%, 15-20% or 20-30% thicker than the wall of the preceding sorbent pouch.

Figure 23:
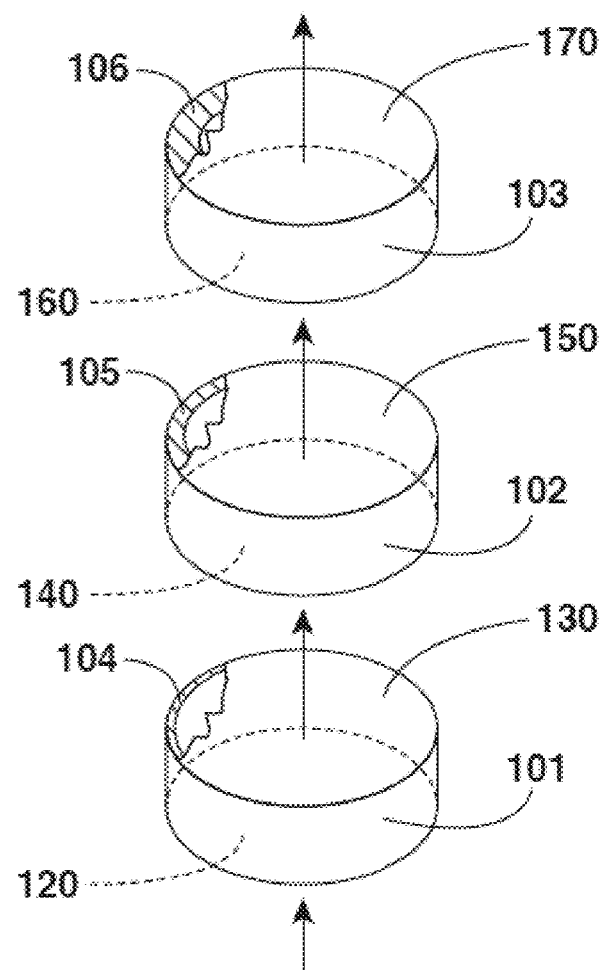
FIG. 23 shows an exploded perspective view of a sorbent cartridge having stacked sorbent pouches, with each sorbent pouch in series having a thicker sidewall, and therefore smaller interior diameter, than that of the previous sorbent pouch

FIG. 23 is an exploded view of FIG. 22. As can be seen, fluid flowing up through the first sorbent pouch 101 through sorbent pouches 102 and 103 will be pushed toward the center of each sorbent pouch by the thickening side walls of each sorbent pouch in series.

Figure 24:
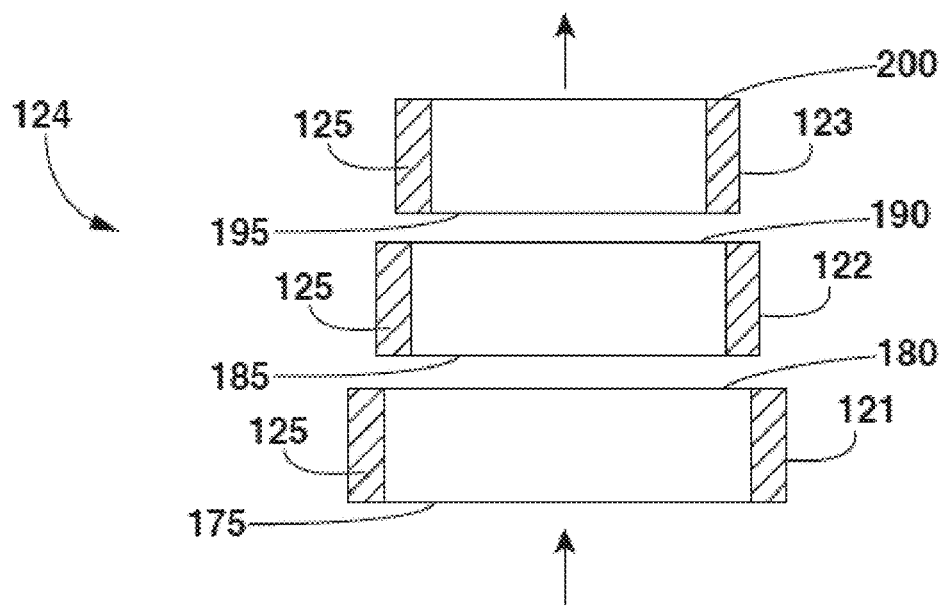
FIG. 24 shows an exploded cross-sectional view of a sorbent cartridge having stacked sorbent pouches, with each sorbent pouch in series having a smaller diameter than that of the previous sorbent pouch.

In any embodiment of the first or second aspect of the invention, each sorbent pouch may be constructed with a smaller outside diameter than that of the preceding sorbent pouch. Constructing each sorbent pouch with a smaller diameter and the same wall thickness as the previous sorbent pouch will create the same effect as constructing each sorbent pouch with a progressively thicker wall. In any embodiment of the first or second aspect of the invention, as shown in FIG. 24, the interior diameter of the sorbent cartridge 124 can also decrease to accommodate each sorbent pouch. The first sorbent pouch 121 can have the largest diameter of all the sorbent pouches and can be placed in the sorbent cartridge 124 where the interior diameter of the sorbent cartridge 124 is the largest. Second sorbent pouch 122 can have a smaller diameter than first sorbent pouch 121 and can be placed in the sorbent cartridge 124 where the interior diameter of the sorbent cartridge 124 is smaller. Third sorbent pouch 123 can have a smaller diameter than second sorbent pouch 122 and can be placed in the sorbent cartridge 124 where the interior diameter of the sorbent cartridge 124 is smallest. The wall thickness 125 of each sorbent pouch can be constant. In any embodiment of the first or second aspect of the invention, more than three sorbent pouches can be used, and the sorbent cartridge 124 can have more than three different sized interior diameters. In any embodiment of the first or second aspect of the invention, fluid can flow up through bottom surface 175 and top surface 180 of first sorbent pouch 121, through bottom surface 185 and top surface 190 of second sorbent pouch 122, and through bottom surface 195 and top surface 200 of third sorbent pouch 123 such that the fluid is passing through a constricting area with each subsequent sorbent pouch, and accordingly is pushed toward the center of each sorbent pouch.

Figure 25:
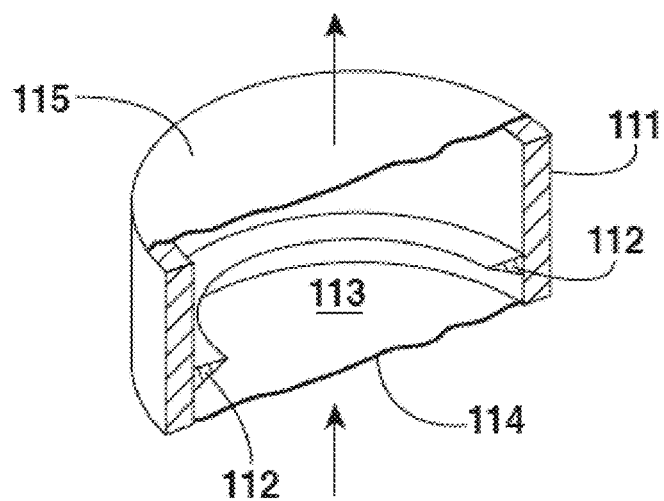
FIG. 25 shows a cross-sectional perspective view of a sorbent pouch having an annular ring disposed on the interior circumference of the sorbent pouch.

In any embodiment of the first or second aspect of the invention, as shown in FIG. 25, annular rings or "o-rings" may be used to direct flow of fluid into the center of the sorbent pouch. A sorbent pouch 111 can have an annular ring 112 placed and adhered by any known means around the interior circumference of the sorbent pouch 111. The cross-section of the annular ring 112 can be angled so that the annular ring 112 extends radially into the interior 113 of the sorbent pouch 111. The angle of the annular ring 112 can direct fluid entering the bottom 114 of the sorbent pouch 111 from the area near the edge of the sorbent pouch 111 into the interior 113 of the sorbent pouch 111 as the fluid exits through the top surface 115 of the sorbent pouch 111. In any embodiment of the first or second aspect of the invention, the annular ring can have a curved shape. In any embodiment of the first or second aspect of the invention, the annular ring can have a rectangular shape. In any embodiment of the first or second aspect of the invention, each sorbent pouch can include multiple annular rings. For example, a sorbent pouch may have 2, 3, 4, 5, 6 or more annular rings spaced along the interior circumference of the sorbent pouch to continuously push fluid into the center of the sorbent pouch as the fluid passes through the sorbent pouch. The annular rings may be made out of any substance known in the art. In any embodiment of the first or second aspect of the invention, the annular rings may be constructed from an elastomeric material, such as the o-rings described above. In any embodiment of the first or second aspect of the invention, the annular rings may be constructed from plastic or some other inert material. In any embodiment of the first or second aspect of the invention, the annular rings may extend inwardly towards the center of the sorbent pouch at a length of between 5-10% of the diameter of the sorbent pouch. In any embodiment of the first or second aspect of the invention, the annular rings may extend between 1-5%, 10-15%, 15-20% or 20-30% of the diameter of the sorbent pouch.

Figure 20:
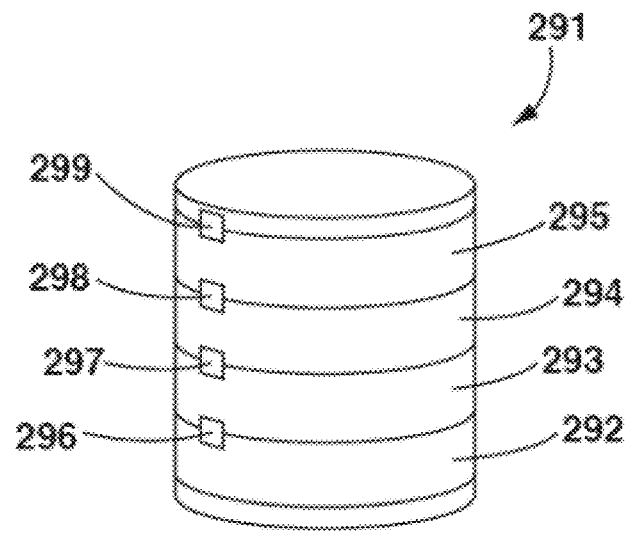
FIG. 20 is a perspective view of a sorbent cartridge comprising sorbent pouches containing activated carbon, hydrous zirconium oxide, urease, alumina, and zirconium phosphate with sensors placed within the sorbent cartridge between each sorbent pouch to monitor the content of the spent dialysate.

In any embodiment of the first or second aspect of the invention, sensors may be deployed in a sorbent cartridge after or between the sorbent pouches to ensure that fluid is properly passing through the sorbent pouch and that the sorbent material within the sorbent pouch is properly removing or converting the toxins present in the spent dialysate. For example, as shown in FIG. 20, a sorbent cartridge 291 can comprise a sorbent pouch containing activated carbon 292, a sorbent pouch containing hydrous zirconium oxide 293, a sorbent pouch containing alumina and urease 294, and a sorbent pouch containing zirconium phosphate 295. The sorbent pouches can be placed in any order. For example, the first sorbent pouch 292 can contain activated carbon, the second sorbent pouch 293 can contain alumina and urease, the third sorbent pouch 294 can contain hydrous zirconium oxide and the fourth sorbent pouch 295 can contain zirconium phosphate. In any embodiment of the first or second aspect of the invention, the first sorbent pouch 292 can contain alumina and urease, the second sorbent pouch 293 can contain hydrous zirconium oxide, the third sorbent pouch 294 can contain zirconium phosphate and the fourth sorbent pouch 295 can contain activated carbon. Any order of sorbent materials is envisioned, so long as a sorbent pouch containing zirconium phosphate is positioned downstream from any sorbent pouch containing urease. Further, any sorbent pouch can contain multiple sorbent materials, either arranged in layers or intermixed as described above, thus allowing for the use of less sorbent pouches. A sensor 296 can be placed after the sorbent pouch containing activated carbon 292 to test the spent dialysate for toxins that are normally removed by activated carbon, such as β-2 microglobulin or creatinine. Another sensor 297 can be deployed after the sorbent pouch containing hydrous zirconium oxide 293 to test the spent dialysate for the presence of phosphates or fluoride ions. A third sensor 298 can be deployed after the alumina and urease containing sorbent pouch 294 to test for the presence of urea. A fourth sensor 299 can be deployed after the zirconium phosphate containing sorbent pouch 295 to test for the presence of ammonia. In any embodiment of the first or second aspect of the invention the sensors can be conductivity sensors. Although FIG. 20 shows four sensors being used, the first or second aspect of the invention contemplates using any number of sensors, including more or less than four. The presence of additional compounds that may be present in spent dialysate can be tested, and the presence of all of the compounds described above need not be tested.

In any embodiment of the first or second aspect of the invention, two or more sorbent pouches containing the same sorbent material can be used. For highly uremic or particularly large patients, more of a given sorbent material may be necessary. In such cases, a second sorbent pouch containing, for example, zirconium phosphate, may be used in the system. This would give the patient twice as much of the sorbent material, allowing the removal of a greater amount of a given toxin or toxins in a single uninterrupted dialysis session.

In any embodiment of the first or second aspect of the invention, the sorbent pouches of the present invention may themselves be separated across two or more modules as described above. This can provide for further segregation of sorbent materials, and allow for easier recharging and/or disposal of some of the sorbent pouches, while not affecting other sorbent pouches.

By providing each sorbent material, or combinations of sorbent materials, within a single sorbent packaging, easily customizable sorbent regeneration systems are made possible. Flexible packaging, wherein fluid can pass freely into the sorbent material, but the sorbent materials cannot move out, can allow for patients with different needs to utilize different dialysate regeneration systems within a single dialysis machine or type of dialysis machine.

Figure 21:
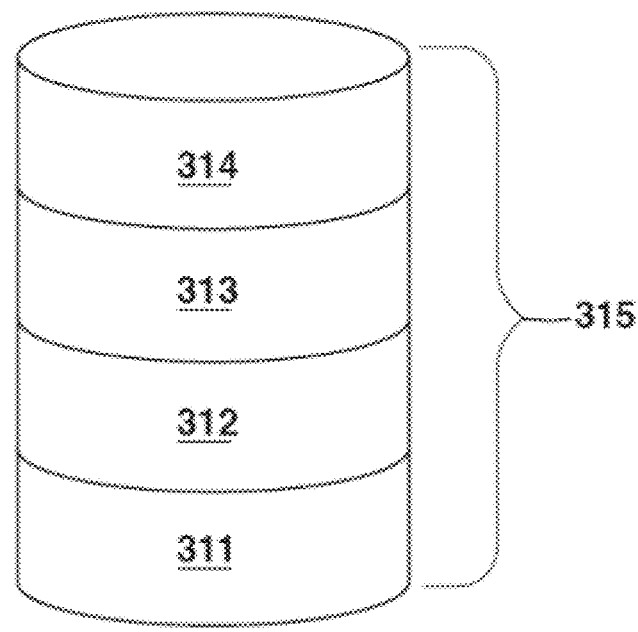
FIG. 21 is a perspective view of a stacked sorbent pouch assembly.

In any embodiment of the first or second aspect of this invention, as shown in FIG. 21, sorbent pouches can fit directly together in order to create a unitary structure. Sorbent pouch 311, which can contain activated carbon, can attach directly to sorbent pouch 312 that can contain hydrous zirconium oxide, as described in FIG. 2. Sorbent pouch 312 can attach directly to sorbent pouch 313, which can contain alumina and urease. Sorbent pouch 313 can attach directly to sorbent pouch 314, which can contain zirconium phosphate. The particular order of sorbent pouches is flexible. For example, sorbent pouch 311 can contain activated carbon, sorbent pouch 312 can contain alumina and urease, sorbent pouch 313 can contain hydrous zirconium oxide, and sorbent pouch 314 can contain zirconium phosphate. In any embodiment of the first or second aspect of the invention, sorbent cartridge 311 can contain activated carbon, sorbent pouch 312 can contain alumina and urease, sorbent pouch 313 can contain zirconium phosphate and sorbent pouch 314 can contain hydrous zirconium oxide. Any order of sorbent materials is contemplated within the invention, so long as any sorbent pouch containing zirconium phosphate is located downstream of any sorbent pouch containing urease. In any embodiment of the first or second aspect of the invention, multiple sorbent materials can be placed in a single sorbent pouch, either arranged in layers or intermixed. The result is sorbent cartridge 315, which is a unitary structure without an external housing.

Because the sorbent pouches can fit together, with no need for an external housing, it is possible for different sizes of sorbent pouches to fit together, such as the sizes shown in FIG. 1. For instance, sorbent pouch 311 in FIG. 21 can be made of a height larger or smaller than shown. So long as the top and bottom portions of the sorbent pouch 311 are the same size, any size sorbent pouch can be utilized in the dialysate regeneration system. This allows for an easily customizable sorbent regeneration system, wherein the amount of each sorbent material can be based on the particular needs of the user. This reduces costs and wastes associated with non-customizable dialysate regeneration systems.

One skilled in the art will understand that various combinations and/or modifications and variations can be made in the stacked sorbent assembly depending upon the specific needs for operation. Moreover, features illustrated or described as being part of the invention can be included in the invention, either alone or in combination.

We claim:

1. A modular dialysate regeneration assembly, comprising:
   a sorbent cartridge comprising a plurality of sorbent compartments each containing at least one sorbent material wherein each of the plurality of sorbent compartments are attachable to another sorbent compartment to form the modular dialysate regeneration assembly; and
   a processor programmed to determine an amount and type of sorbent material in each sorbent compartment for a patient, the modular dialysate regeneration assembly having a desired dialysate regeneration profile based on one or more dialysis parameters and/or one or more patient parameters wherein the processor determines the amount and type of sorbent material in each sorbent compartment of the dialysate regeneration profile based on the dialysis parameters and/or the patient parameters.

2. The modular dialysate regeneration assembly of claim 1, wherein the plurality of sorbent compartments have one or more sizes wherein any sized sorbent compartment is attachable to any other sized sorbent compartment.

3. The modular dialysate regeneration assembly of claim 1, wherein at least one of the plurality of sorbent compartments has a circular or rectangular planar base having a wall extending perpendicularly and upwardly from said base defining an internal area; and
   a circular or substantially rectangular planar top matching the planar base wherein the sorbent compartment has an engagement configuration selected from any one of:
   (i) the base cooperatively engaging with the top of another sorbent compartment and the top cooperatively engaging with the base of another sorbent compartment;
   (ii) the base not cooperatively engaging with the top of another sorbent compartment and the top cooperatively engaging with the base of another sorbent compartment;
   (iii) the base cooperatively engaging with the top of another sorbent compartment and the top not cooperatively engaging with the base of another sorbent compartment; and
   (iv) the base not cooperatively engaging with the top of another sorbent compartment and the top not cooperatively engaging with the base of another sorbent compartment.

4. The modular dialysate regeneration assembly of claim 1, wherein the plurality of sorbent compartments are selected from any combination or number of compartments from a selected group of:
   (i) a first sorbent compartment having a sorbent weight ranging from 0.1 kg to 0.5 kg;
   (ii) a second sorbent compartment having a sorbent weight ranging from 0.5 kg to 1.0 kg;
   (iii) a third sorbent compartment having a sorbent weight ranging from 1.0 kg to 1.5 kg;
   (iv) a fourth sorbent compartment having a sorbent weight ranging from 1.5 kg to 2.0 kg;
   (v) a fifth sorbent compartment having a sorbent weight ranging from 2.0 kg to 2.5 kg;
   (vi) a sixth sorbent compartment having a sorbent weight ranging from 2.5 kg to 3.0 kg;
   (vii) a seventh sorbent compartment having a sorbent weight ranging from 3.0 kg to 3.5 kg;
   (viii) an eighth sorbent compartment having a sorbent weight ranging from 3.5 kg to 4.0 kg;
   (ix) a ninth sorbent compartment having a sorbent weight ranging from 4.0 kg to 4.5 kg;
   (x) a tenth sorbent compartment having a sorbent weight ranging from 4.5 kg to 5.0 kg; and
   (xi) an eleventh sorbent compartment having a sorbent weight ranging from 0.0001 kg to 0.1 kg.

5. The modular dialysate regeneration assembly of claim 1, wherein the plurality of sorbent compartments are selected from any combination or number of compartments from a selected group of:
   (i) a first sorbent compartment having a volume ranging from 0.25 L to 1.3 L;
   (ii) a second sorbent compartment having a volume ranging from 1.3 L to 2.5 L;
   (iii) a third sorbent compartment having a volume ranging from 2.5 L to 3.7 L;
   (iv) a fourth sorbent compartment having a volume ranging from 3.7 L to 5.0 L;
   (v) a fifth sorbent compartment having a volume ranging from 5.0 L to 6.3 L;
   (vi) a sixth sorbent compartment having a volume ranging from 6.3 L to 7.5 L;
   (vii) a seventh sorbent compartment having a volume ranging from 7.5 L to 10 L;
   (viii) an eighth sorbent compartment having a volume ranging from 0.01 L to 0.25 L; and
   (ix) a ninth sorbent compartment having a volume ranging from 0.001 L to 0.01 L.

6. The modular dialysate regeneration assembly of claim 1, wherein the at least one of the sorbent compartments has a planar base with upwardly extending walls connecting to a planar top wherein the walls are constructed from a rigid, fluid impermeable material.

7. The modular dialysate regeneration assembly of claim 6, wherein either:
   the base and top are circular and wherein the upwardly extending walls slope inward to an axis of the compartment wherein the top has a smaller surface area than the base or the upwardly extending walls slope outward from the axis wherein the top has a larger surface area than the base; or the base and top are rectangular having four upwardly extending walls sloping inward to an axis of the compartment wherein the top has a smaller surface area than the base or four upwardly extending walls sloping outward from the axis wherein the top has a larger surface area than the base.

8. The modular dialysate regeneration assembly of claim 6, further comprising one or more of:
   (i) an engagement member disposed on and extending upwardly from the planar top of the sorbent compartment;
   (ii) a receiving groove disposed on the planar base of the sorbent compartment for receiving an engagement member;

(iii) an engagement member disposed on and extending downwardly from the planar base of the sorbent compartment; or
(iv) a receiving groove disposed on the planar top of the sorbent compartment for receiving an engagement member.

9. The modular dialysate regeneration assembly of claim 1 wherein the sorbent materials are selected from a group comprising activated carbon, ion exchange resin, hydrous zirconium oxide, alumina, urease, a mixture of alumina and urease, zirconium phosphate, and any combination thereof.

10. The modular dialysate regeneration assembly of claim 1 wherein the one or more dialysis parameters and/or one or more patient parameters are selected from a group comprising patient weight, concentration of one or more compounds in a blood sample from a patient, previous dialysis results of the patient, dialysis rate, length of dialysis session, a level of impurities in the water used, an expected amount of infusates to be added, and combinations thereof.

11. The modular dialysate regeneration assembly of claim 1, wherein the sorbent compartments are sorbent pouches configurable into a stacked assembly of the sorbent pouches wherein each of the sorbent pouches is constructed in-part of a porous material forming the pouch containing inside the at least one sorbent material wherein the porous material allows fluid to pass through the sorbent pouch and substantially retains the at least one sorbent material in the sorbent pouch.

12. The modular dialysate regeneration assembly of claim 11 wherein the sorbent pouch is constructed from a material selected from a group comprising bolting cloth, porous polymer, porous metal, cotton, ashless filter paper, Dacron and polyethylene terephthalate.

13. The modular dialysate regeneration assembly of claim 1, wherein each of the sorbent compartments is a distinct color depending on the sorbent material contained within the sorbent compartment.

14. The modular dialysate regeneration assembly of claim 3, wherein at least one of the sorbent compartments contains urease and at least one of the sorbent compartments contains zirconium phosphate; wherein the engagement configuration is such that the compartment containing urease can connect to the compartment containing zirconium phosphate, wherein the compartment containing urease is positioned immediately before the compartment containing zirconium phosphate; and wherein the engagement configuration is such that the top of the compartment containing urease cannot cooperatively engage with any sorbent compartment except the sorbent compartment containing zirconium phosphate and the bottom of the compartment containing zirconium phosphate cannot cooperatively engage with any sorbent compartment except the sorbent compartment containing urease.

15. The modular dialysate regeneration assembly of claim 1, wherein each of the plurality of sorbent compartments comprises one or more selected from:

(i) sidewalls having a thickness different from the sidewall thicknesses of the other sorbent compartments, such that the one or more sorbent compartments have differing interior diameters; wherein each sorbent compartment has a sidewall thickness greater than that of the previous sorbent compartment in series;
(ii) differing exterior diameters; wherein each sorbent compartment has an exterior diameter smaller than that of the previous sorbent compartment in series; or
(iii) one or more annular ring, wherein the one or more annular ring is constructed from a fluid impermeable substance; wherein the one or more annular ring is disposed on the interior circumference of each of the one or more sorbent compartments and extends radially into the center of each of the one or more sorbent compartments; and wherein the annular ring has a cross sectional shape selected from the group comprising circular, triangular, and rectangular.

16. The modular dialysate regeneration assembly of claim 1, wherein the processor displays the amount of the at least one sorbent material needed for a particular dialysis session based upon the one or more dialysis parameters and/or the patient parameters.

17. The modular dialysate regeneration assembly of claim 16, wherein the processor is programmed to receive the one or more dialysis parameters and/or patient parameters from a user.

18. The modular dialysate regeneration assembly of claim 1, wherein the at least one sorbent material is selected from the group consisting of zirconium phosphate, zirconium oxide, urease, activated carbon, ion-exchange resin, and combinations thereof.

19. The modular dialysate regeneration assembly of claim 1, wherein the processor is programmed to determine initially a necessary amount of the at least one sorbent material needed for treatment and to determine an updated amount of the at least one sorbent material based on the dialysis parameters and/or the patient parameters.

20. The modular dialysate regeneration assembly of claim 1, wherein plurality of sorbent compartments form a unitary structure.

21. The modular dialysate regeneration assembly of claim 1, wherein the processor is programmed to determine a correct number of the one or more attachable sorbent compartments based on the amount of the at least one sorbent material needed for treatment.

22. The modular dialysate regeneration assembly of claim 21, wherein the processor is programmed to determine the correct number of the one or more attachable sorbent compartments and correct amount of the at least one sorbent material needed for treatment based on one or more internal tables and to update the one or more internal tables based on a remaining capacity of the one or more sorbent materials after a dialysis session.

\* \* \* \* \*